United States Patent
Thomas

(10) Patent No.: US 10,617,974 B2
(45) Date of Patent: Apr. 14, 2020

(54) METHOD AND APPARATUS FOR EXTRACTING BOTANICAL OILS

(71) Applicant: Natural Extraction Systems, LLC, Boulder, CO (US)

(72) Inventor: C. Russell Thomas, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 16/098,265

(22) PCT Filed: May 2, 2017

(86) PCT No.: PCT/US2017/030557
§ 371 (c)(1),
(2) Date: Nov. 1, 2018

(87) PCT Pub. No.: WO2017/192527
PCT Pub. Date: Nov. 9, 2017

(65) Prior Publication Data
US 2019/0151771 A1 May 23, 2019

Related U.S. Application Data

(60) Provisional application No. 62/330,522, filed on May 2, 2016.

(51) Int. Cl.
*B01D 11/02* (2006.01)
*B01D 45/12* (2006.01)
(Continued)

(52) U.S. Cl.
CPC ............ *B01D 11/0296* (2013.01); *B01D 1/14* (2013.01); *B01D 3/34* (2013.01); *B01D 3/346* (2013.01); *B01D 3/38* (2013.01); *B01D 3/40* (2013.01); *B01D 5/00* (2013.01); *B01D 5/0003* (2013.01); *B01D 5/0042* (2013.01); *B01D 5/0072* (2013.01); *B01D 11/00* (2013.01); *B01D 11/028* (2013.01); *B01D 11/0288* (2013.01); *B01D 45/12* (2013.01); *C07C 37/685* (2013.01);
(Continued)

(58) Field of Classification Search
CPC ........ B01D 11/0296; B01D 1/14; B01D 3/34; B01D 3/38
USPC .......................................................... 554/21
See application file for complete search history.

(56) References Cited

U.S. PATENT DOCUMENTS 2,467,435 A 4/1949 Langhurst
2,805,981 A 9/1957 Calvin et al.
(Continued)

FOREIGN PATENT DOCUMENTS

CN 201643760 U 11/2010
CN 101553702 B 6/2012
(Continued)

*Primary Examiner* — Deborah D Carr
(74) *Attorney, Agent, or Firm* — Dinsmore & Shohl LLP

(57) ABSTRACT

Various aspects of the disclosure relate to methods and systems for extracting oil from plant material. A system may comprise a gas moving device, an extraction chamber, and a condensation surface. Oil of the plant material may be volatized in the extraction chamber and then propelled by the gas moving device to the condensation surface to be collected. In various embodiments, the systems and methods allow the extraction of oil from plant material with little or no solvent.

23 Claims, 18 Drawing Sheets

(51) Int. Cl.
  *B01D 5/00* (2006.01)
  *B01D 3/34* (2006.01)
  *B01D 3/40* (2006.01)
  *B01D 3/38* (2006.01)
  *B01D 11/00* (2006.01)
  *B01D 1/14* (2006.01)
  *C07C 37/68* (2006.01)
  *C07C 37/72* (2006.01)
  *C07D 311/80* (2006.01)
  *C11B 1/10* (2006.01)
  *B01D 45/16* (2006.01)

(52) U.S. Cl.
  CPC ............ *C07C 37/72* (2013.01); *C07D 311/80* (2013.01); *C11B 1/10* (2013.01); *B01D 45/16* (2013.01)

(56) References Cited

U.S. PATENT DOCUMENTS

| | | |
|---|---|---|
| 3,270,437 A | 9/1966 | Lara et al. |
| 4,227,997 A | 10/1980 | Shaddock |
| 4,279,824 A | 7/1981 | McKinney |
| 4,396,487 A | 8/1983 | Strumskis |
| 4,752,307 A | 6/1988 | Asmus et al. |
| 5,026,549 A | 6/1991 | Coutiere |
| 5,235,992 A | 8/1993 | Sensabaugh, Jr. |
| 5,408,924 A | 4/1995 | Arendt et al. |
| 6,019,819 A | 2/2000 | Williams |
| 6,248,910 B1 | 6/2001 | Franke |
| 6,403,126 B1 | 6/2002 | Webster et al. |
| 6,860,998 B1 | 3/2005 | Wilde |
| 7,001,502 B1 | 2/2006 | Satchwell et al. |
| 7,344,736 B2 | 3/2008 | Whittle et al. |
| 7,622,140 B2 | 11/2009 | Whittle et al. |
| 7,833,298 B2 | 11/2010 | Larnholm et al. |
| 8,062,410 B2 | 11/2011 | Bullinger et al. |
| 8,329,229 B2 | 12/2012 | Gonzalez et al. |
| 8,343,553 B2 | 1/2013 | Hospodor |
| 8,445,034 B1 | 5/2013 | Coles, Jr. |
| 9,038,413 B2 | 5/2015 | Howard et al. |
| 2002/0139097 A1* | 10/2002 | Brilmaker ............... B01D 45/14 55/456 |
| 2004/0049059 A1 | 3/2004 | Mueller |
| 2004/0147767 A1 | 7/2004 | Whittle et al. |
| 2004/0147769 A1 | 7/2004 | Davis |
| 2005/0172802 A1* | 8/2005 | Betting ............... B01D 47/06 95/29 |
| 2009/0054711 A1 | 2/2009 | Lawrence et al. |
| 2010/0119606 A1 | 5/2010 | Whittle et al. |
| 2011/0119606 A1* | 5/2011 | Abe ........................ G06F 9/454 715/763 |
| 2011/0133120 A1 | 6/2011 | McGhee |
| 2013/0240347 A1 | 9/2013 | Hackleman et al. |
| 2014/0001027 A1 | 1/2014 | Balass |
| 2014/0113010 A1 | 4/2014 | Hospodor et al. |
| 2014/0193303 A1 | 7/2014 | Ellis et al. |
| 2015/0252286 A1 | 9/2015 | Scialdone et al. |

FOREIGN PATENT DOCUMENTS

| | | | |
|---|---|---|---|
| EP | 2644039 A1 | 10/2013 | |
| GB | 635121 | 10/1945 | |
| JP | 4388715 | 11/2002 | |
| JP | 4849578 B1 | 1/2012 | |
| WO | WO-2014/000077 A1 | 1/2014 | |
| WO | WO-2014000077 A1 * | 1/2014 | ............ A61K 36/61 |
| WO | WO-2015/049585 A2 | 4/2015 | |
| WO | WO-2015049585 A2 * | 4/2015 | ............... B01D 1/14 |

\* cited by examiner

METHOD AND APPARATUS FOR EXTRACTING BOTANICAL OILS

CROSS REFERENCE TO RELATED APPLICATION

This application is the U.S. national phase under 35 U.S.C. § 371 of International Application No. PCT/US2017/030557, filed May 2, 2017, which claims priority to U.S. provisional application No. 62/330,522, filed May 2, 2016. The entire content of both of which is incorporated herein by reference.

SUMMARY OF THE INVENTION

The present invention consists of a system of parts and processes that are used to extract botanical oils, terpenoids, oleoresins and/or resins (generically referred to in this disclosure as "oils" or "plant oils") from plant material or an oil containing substrate (generically referred to in this disclosure as "plant material"). The method of extraction includes contacting the plant material with a heated gas and/or heated surface of a specific temperature such that the oils contained within the plant material are caused to volatilize and leave the plant material in the form of a vapor. The vapor is then condensed and collected using a collection solvent in a manner that preserves and protects the integrity of the oil constituents. The collection solvent utilized in the system is preferably ethanol or a mixture of ethanol and water, however, water, chloroform or a number of other suitable organic or inorganic solvents may be utilized to attain the desired results. A method of separating the captured plant oils from the collection solvent is included whereby a substantially purified plant oil extract can be obtained as a final product of the system.

As non-limiting examples, a few of the many types of plant materials that may be processed using the present invention may include various forms of hemp or cannabis that may generally be classified as *Cannabis sativa, Cannabis indica, Cannabis ruderalis*, hybridized crosses of various species or families of cannabis, or a mixture of one or more types of cannabis and/or other plant material. When cannabis is selected as the plant material to be processed, the preferred oils to be extracted may include the various chemical forms of cannabidiol (CBD), cannabidivarin (CBDV), delta-9-tetrahydrocannabinol (THC), delta-8-tetrahydrocannabinol, tetrahydrocannabivarin (THCV), cannabinol (CBN), cannabigerol, cannabichromene, chemically converted cannabinoids or any other cannabinoid. Other valuable terpenoid oils that may be extracted from cannabis may include the various chemical forms of linalool, caryophyllene, myrcene, limonene, humulene, pinene. By manipulating the temperature of the heated gas and/or heated surfaces that contact the plant materials and completing successive extraction cycles, it is possible to isolate the various plant oils into substantially purified fractions. It is also possible utilize a wider temperature band to extract a range of plant oils in a single extraction cycle. It should be noted that any plant material may be processed by the present invention and any plant oils may be targeted as the oils to be extracted.

An embodiment of the present invention provides a system for extracting an oil from plant material. A gas moving device is operable to propel a gas stream through the system, the gas stream being a stream of air or gas with or without entrained vapor, solids or droplets of liquid therein. An extraction chamber is in communication with the gas moving device such that the gas stream is directed through the extraction chamber, the extraction chamber operable to volatize at least a portion of an oil from a plant material such that the volatilized oil is disposed in the gas stream as an extracted oil. A collection chamber is in communication with the extraction chamber such that the gas stream flows through the collection chamber, the collection chamber having collection solvent operable to collect at least a portion of the extracted oil from the gas stream. A liquid collector in fluid communication with the collection chamber for collecting at least a portion of the collection solvent and extracted oil.

Some versions include a heater disposed such that the gas stream flows through the heater and the gas stream is heated. The heater may be operable to heat the gas stream to a temperature sufficient to cause volatilization of the oil to be extracted, with the extraction chamber being in communication with the heater such that the heated gas stream is directed through the receiving area, the extraction chamber operable to volatilize the portion of the oil by the heated gas stream volatilizing the portion of the oil as the heated gas stream flows through the extraction chamber. The extraction chamber may include a volatilization chamber having an upwardly facing entry tube and an exit disposed below the entry tube such that the gas flow impacts an upper end of the volatilization chamber and reverses direction before exiting the volatilization chamber. The extraction chamber may be a modified spray dryer having a nozzle, the heated gas stream with entrained plant material being introduced through the nozzle. In some examples, the heater is operable to heat the gas stream at an exit of the heater or in the extraction chamber to a temperature in the range of 290 to 430 degrees Fahrenheit. In certain examples, the heater is operable to heat the gas stream to a temperature of at least 290 degrees Fahrenheit. The heater may be a tube-in-shell heat exchanger with a steam generator providing steam to the heat exchanger or is an electric heater.

In some versions, the extraction chamber includes a volatilization chamber having at least one heated surface and the portion of the oil is volatilized by the plant material contacting the heated surface. In certain examples, the at least one heated surface has a temperature is in the range of 290 to 430 degrees Fahrenheit. In some examples, the at least one heated surface has a temperature of at least 290 Fahrenheit. The extraction chamber may have a tangential entrance.

In some versions, the extraction chamber includes a flash drying volatilization chamber having an entrance and an exit, the exit being above the entrance such that the gas stream flows upwardly and entrained plant materials are carried upwardly by the gas stream. The entrance may be a nozzle.

In some embodiments, the extraction chamber comprises a volatilization chamber having a tangential entrance.

In some versions, the extraction chamber includes elements to break up clumps of plant material. Examples of such elements include balls, beads and rotating elements.

In some embodiments, the extraction chamber includes an insulated and/or heated shell.

In certain versions, the extraction chamber may include a plurality of volatilization chambers in series and/or parallel.

Some versions of the extraction chamber may have a receiving area for receiving plant material for extraction.

Certain embodiments further include a plant material entrainment zone in communication with the gas stream mover such that the gas stream flows through the plant material entrainment zone, the plant material entrainment zone forming at least a part of the extraction chamber. A hopper for holding plant material and a plant material portioning device operable to introduce the plant material into the plant material entrainment zone may also be included. Examples of the plant material portioning devices include an auger screw, a rotary valve, and a rotary airlock valve.

In some embodiments, the collection chamber has at least one collection solvent sprayer operable to spray droplets of collection solvent into the gas stream such that at least some of the extracted oil dissolves into the collection solvent droplets and at least some of the collection solvent droplets flow to the liquid collector. The at least one collection solvent sprayer may be a plurality of collection solvent sprayers and the collection solvent droplets may generally have a diameter greater than one micron and less than 300 microns. The collection chamber may have packing material disposed therein with the packing material wetted by the collection solvent.

In some embodiments, the system includes a secondary liquid separator in communication with the collection chamber.

In certain embodiments, the system includes a cooling chamber in communication with the extraction chamber such that the heated gas stream flows through the cooling chamber, and the cooling chamber is operable to cool the heated gas stream to or below a volatilization temperature of the extracted oil such that at least some of the extracted oil liquefies into droplets entrained in the gas stream. The collection chamber is downstream of the cooling chamber. The cooling chamber may be a spray cooling chamber having a high pressure sprayer operable to spray collection solvent into the heated gas stream such that the collection solvent rapidly cools the heated gas stream to or below a condensation temperature of the oil. The sprayed collection solvent may be collection solvent and extracted oil from the liquid collector, and the system may further include a pump operable to pump the collection solvent and extracted oil from the liquid collector to the high pressure sprayer. Alternatively, the sprayed collection solvent is a substantially purified collection solvent. A collection solvent cooler may be provided to cool the collection solvent for the high pressure sprayer.

In certain embodiments, interior surfaces of the extraction chamber and portions of the system downstream of the extraction chamber and upstream of the collection and/or cooling chamber are maintained at a temperature sufficient to prevent condensation of the volatilized oils on said interior surfaces. In some examples, the temperature sufficient to prevent condensation is in the range of 290 to 430 degrees Fahrenheit.

Some embodiments include a gas stream cooler in communication with the extraction chamber. The gas stream cooler may be a tube-in-shell heat exchanger.

Some embodiments include an agglomeration chamber in communication with the cooling chamber or extraction chamber so as to receive the gas stream, the agglomeration chamber increasing the droplet size in the gas stream. The agglomeration chamber may have a diameter greater than a diameter of a passage upstream of the agglomeration chamber such that the gas stream slows down in the agglomeration chamber. The agglomeration chamber may include at least one collection solvent vapor injector operable to introduce a collection solvent vapor to the agglomeration chamber.

Alternatively, or additionally, the agglomeration chamber may have a flow of cool gas that mixes with the heated gas stream. An oil/solvent separation system may be provided to generally separate the collection solvent from the extracted oil so as to provide a generally purified collection solvent and a generally purified oil, with the separation system providing collection solvent vapor to the at least one collection solvent vapor injector.

In some embodiments, passages or chambers disposed downstream of the extraction chamber have inner surfaces with a temperature less than a condensation temperature of the collection solvent such that collection solvent vapor entrained in the gas stream condenses on the inner surfaces and forms a solvent liquid that washes accumulated oils and collection solvent containing dissolved oils from the inner surfaces, the combined liquid flowing to the liquid collector. In certain examples, the temperature less than a condensation temperature is in the range of approximately 85 to 145 degrees Fahrenheit. In some examples, interior surfaces of the extraction chamber are heated to a temperature sufficient to prevent condensation of the volatilized oils on the interior surfaces.

Some embodiments include an oil/solvent separation system operable to generally separate the collection solvent from the extracted oil so as to provide a generally purified collection solvent and a generally purified oil. The separation system may include an evaporation device, and may also include a condenser to condense solvent vapor from the evaporation device.

Some embodiments include a plant material separation device in communication with and downstream of the extraction chamber, the plant material separation device operable to separate at least a portion of the plant material entrained in the gas stream therefrom. The plant material separation device may be a cyclone or centrifugal separator and/or the separator has a heated exit and/or the separator has a heated backflow to displace vapors. The plant material separation device may also include a secondary entrainment zone and a secondary gas stream mover operable to propel a secondary gas stream through the secondary entrainment zone, the plant material separation device providing the separated portion of plant material to the secondary entrainment zone. A secondary plant material separator may be in communication with the secondary entrainment zone. In some examples, the secondary gas stream has a temperature less than a temperature of the gas stream flowing through the plant material separation device. A gas stream filter may be in communication with the plant material separation device.

Some embodiments include a collection solvent separation device for separating at least a portion of the collection solvent from the gas stream.

Certain embodiments include a gas pump operable to remove gas from the system so as to maintain an interior pressure below atmospheric and prevent outward leakage from the system.

In some examples, the collection solvent is: a non-toxic, food-grade solvent; a mixture of ethyl alcohol and water; a mixture of organic ethyl alcohol and water; or a solvent containing at least 40% ethyl alcohol. In further examples, the collection solvent is ethanol, a mixture of ethanol and water, water, chloroform or organic or inorganic solvents.

In some embodiments, at least a portion of the collection solvent and extracted oil is recirculated to the collection chamber.

In certain embodiments, the plant materials are raw plant portions or partially processed plant portions and the extracted oil includes terpenoids.

In certain embodiments, the system is a substantially closed loop system.

In some versions, the liquid collector is a sump in fluid communication with at least the collection chamber.

In certain embodiments, the plant materials are raw plant portions or partially processed plant portions and the system is extracting one or more specific saps, resins, oleoresins, lipids, terpenoids or otherwise volatilizable constituents within a plant material that is being processed.

In some embodiments, the gas stream includes a gas selected from air, inert gas, reducing gas and mixtures thereof.

The gas stream mover may be a blower.

The present invention also includes use of any apparatus described herein to provide an extracted oil.

In some versions, the gas moving device is part of the collection chamber.

In some embodiments, the heater and/or the plant material separator and/or the gas stream filter 49 and/or the extraction chamber are insulated and/or heated.

The present invention includes a method for extracting an oil from plant material. Any system described herein may be used. A plant material is provided in the extraction chamber and oil is volatilized from the plant material, the oil being extracted into the gas stream. The gas stream is contacted with a collection solvent such that at least some of the oil is captured by the collection solvent. At least a portion of the oil and collection solvent is collected from the gas stream. In some versions, the plant material is exposed to the heated gas stream, the gas stream being heated to a temperature sufficient to cause volatilization of an oil to be extracted from the plant material.

In some versions of the method, the contacting and collecting steps comprise flowing at least a portion of the gas stream through a collection chamber and spraying the at least a portion of the gas stream with collection solvent such that at least some of the oil in the gas stream is captured by the collection solvent and at least some of the collection solvent flows to the collection chamber.

In some versions of the system or method the plant material is one or more types of cannabis. In some versions, the extracted oil contains one or more of: cannabidiol (CBD); cannabidivarin (CBDV); delta-9-tetrahydrocannabinol (THC); delta-8-tetrahydrocannabinol; tetrahydrocannabivarin (THCV); cannabinol (CBN); cannabigerol; cannabichromene; chemically converted cannabinoids; or other cannabinoids.

In some versions of the system or method, the extraction chamber is operated at a temperature of approximately 315 degrees Fahrenheit.

In some versions of the system or method, the extraction chamber is operated at a temperature of approximately 356 degrees Fahrenheit.

In some versions of the system or method, the extraction chamber is operated at a temperature of approximately 428 degrees Fahrenheit.

Further embodiments and options are described throughout this disclosure.

DETAILED DESCRIPTION OF THE INVENTION

Figure 1:
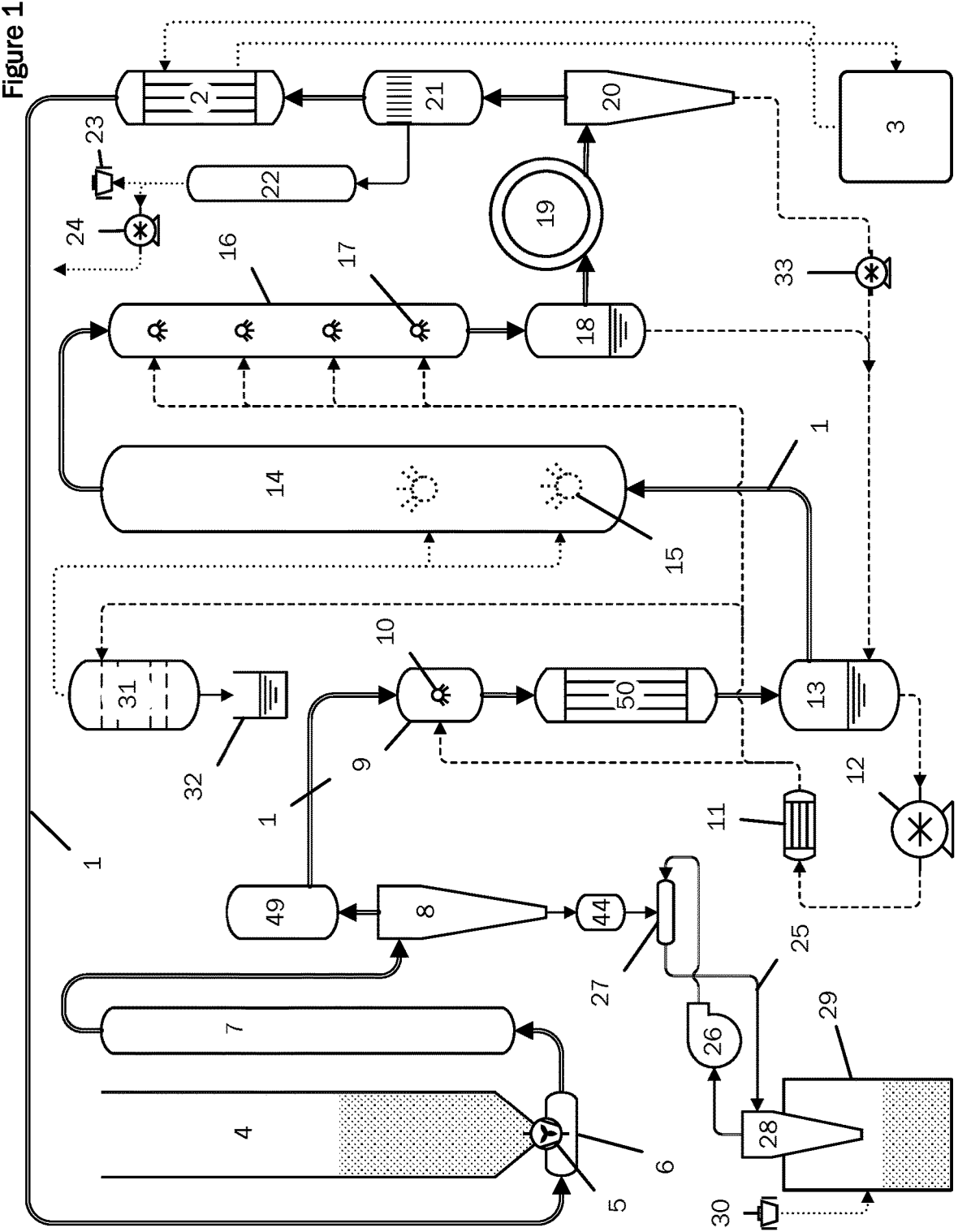
FIG. 1 is a diagrammatic view of an embodiment of the present invention.

FIG. 1 illustrates a diagrammatic view of the primary system parts of an embodiment of the present invention. A system is provided that includes a substantially closed network of passages and chambers containing a moving primary gas stream 1 (generically referred to in this disclosure as the "primary gas stream" or "primary gas flow"), a primary gas stream heater 2, a steam generator 3 to provide a heat source to the primary gas stream heater 2, a plant material or oil containing substrate hopper 4, a plant material portioning device 5, a primary plant material entrainment zone 6, a plant material volatilization chamber 7, a primary plant material separation device 8, an optionally heated separated plant material exit 44, a gas stream filter 49, a cooling and condensation section 9 for contacting the primary gas stream with a cooling collection solvent spray 10, a solvent spray cooler 11, a gas stream cooler 50, a primary pump 12 to provide pressurized collection solvent to various parts of the system, a sump area 13 to store collection solvent and separate collection solvent from the gas stream, an agglomeration chamber 14, a collection solvent vapor/steam introduction method 15, a collection chamber 16 for contacting the primary gas stream with a pressurized spray of collection solvent 17, a separation device or chamber 18 to remove a portion of the collection solvent spray from the primary gas stream 1, a primary gas stream mover 19, a collection solvent droplet separation device 20, a primary gas stream demister/polishing device 21, a collection solvent condenser 22, an out-only check valve 23 allowing gas to pass from the collection solvent condenser to the atmosphere, an air pump 24 capable of removing a portioned amount of gas from the system, a secondary gas stream (generically referred to in this disclosure as the "secondary gas stream" or "secondary gas flow"), a secondary gas stream mover 26, a secondary plant material entrainment zone 27, a secondary plant material separation device 28, a processed plant material collection bin 29, an in-only check valve 30 to allow atmospheric air or a displacing gas into the system via the plant material collection bin 29, a thin film evaporator 31 or similar rapid evaporation device and a plant oil extract/final product collection container 32. Depending on the desired application, any of these components and parts may be duplicated within the system one or more times in series or in parallel or may eliminated entirely to attain different effects. The order of the components within the system may also be modified to attain different effects.

The primary gas stream 1 is propelled through the system by the primary gas stream mover 19. The primary gas stream may consist of atmospheric air, an inert gas such as but not limited to nitrogen, a reducing gas such as but not limited to CO2 or any other suitable gas or mixture. The primary gas stream mover 19 is preferably a regenerative blower, turbo blower, pressure blower or other form of centrifugal blower, however, the primary gas stream mover may consist of any mechanism or method capable of moving a gas. The gas stream may be kept above, below or equal to atmospheric pressure as required for different applications or effects. As the primary gas stream moves through the system, it passes through the primary gas stream heater 2. The primary gas stream heater is preferably a tube-in-shell heat exchanger that receives its heat in the form of saturated steam of a specific pressure and temperature provided by a steam generator 3 system, however, dry steam, a heated gas or other forms of heat exchange may be used, including but not limited to utilizing a hot oil or thermal fluid system whereby a heated fluid is pumped through the heat exchanger. Other forms of steam, gas or fluid powered heat exchangers may also be used as the application requires. Alternatively, the primary gas stream heater may use electric heating elements of various designs to heat the gas stream, including, but not limited to, star-wound heating coil designs. As the primary gas stream passes through the primary gas stream heater 2, the primary gas stream is heated to a temperature that is suitable to volatize one or more of the plant oil constituents present in the plant material.

After being heated, the primary gas stream 1 passes through a primary plant material entrainment section 6 of the system. The plant material supply is located in a hopper section 4 of the system. A portioned amount of plant material is introduced to the primary plant material entrainment section 6 via an auger screw, a rotary valve, a rotary airlock valve or any other suitable distribution mechanism 5. The plant material is preferably introduced to the system in a finely shredded or powdered form, however, other consistencies may also be used depending on what is most preferable in different applications. The plant material may be ground to the ideal or suitable consistency externally, or an integral grinder may be incorporated into the hopper 4, portioning device 5 or entrainment section 6 system as described in, but not in any way limited by, PCT/IB2014/002383. As non-limiting examples, a few of the many types of plant materials that may be processed using the present invention may include various forms of hemp or cannabis that may generally be classified as *Cannabis sativa, Cannabis indica, Cannabis ruderalis*, hybridized crosses of various species or families of cannabis, or a mixture of one or more types of cannabis and/or other plant material. It should be noted that any plant material may be processed by the present invention and any plant oils may be targeted as the oils to be extracted.

As the plant material is introduced to the primary entrainment section 6, the plant material becomes entrained in the heated primary gas stream 1. The entrained plant material travels with the primary gas stream into one or more volatilization chambers 7 placed in series or in parallel. The primary entrainment zone and the volatilization chamber/chambers may together define an extraction chamber and, in some embodiments, may be integrated with one another. Several methods may be used to achieve volatilization of the plant materials within the volatilization chamber, and this invention is not limited to any specific method of volatilization. A preferred way to volatilize the plant materials may be to use a form of pneumatic flash drying, however, adaptations of spray drying, spin drying, pneumatic ring drying, spin dryers with agitators, dryers with classifiers, dryers with agitators, bed drying, any of the volatilization methods proposed in the figures or text of this disclosure or any other method suitable to volatilize the plant materials may be used. Each of these methods will be known to those who are skilled in the art of drying food products, pharmaceutical products and industrial materials, however, the way that this invention is using these methods is unique. A detailed view of several embodiments of the volatilization chamber 7 is illustrated in FIGS. 3, 4, 5, 6, 7, 8*a* and 8*b*, and will be discussed in greater detail in the following sections of this disclosure.

Inside of some versions of the volatilization chamber 7, the plant material is agitated and circulated while being exposed to the heated primary gas stream to cause rapid volatilization of particular plant oils that volatilize near, at or below the temperature maintained within the volatilization chamber by the primary gas stream. In other embodiments, the plant material is forced into contact with a heated surface within the volatilization chamber. The temperature of the gas stream exiting the heater 2 may be adjusted to maintain a desired temperature in the volatilization chamber/s and to counteract any temperature losses as the gas stream travels from the heater 2 to the volatilization chamber/s 7. As will be discussed in detail in other sections of this disclosure, in some embodiments it is also possible to directly heat the volatilization chamber. In most embodiments, targeting a specific temperature within the volatilization chamber will volatilize plant oil compounds that volatilize near or below such a temperature. In order to isolate separate oil compounds, a method of successively processing the plant material at increasing temperatures over multiple extraction cycles may be used to fractionally isolate specific oils or specific groups of oils. Alternatively, a sufficiently high temperature may be selected to volatilize a range of targeted plant oils in a single extraction cycle. Such methods will be well understood by those of skill in the art. In some applications, it may be preferable to exclude a dedicated volatilization chamber from the system if a sufficient volatilization function can be obtained in the primary plant material separator 8. This is discussed in greater detail in a following section.

When cannabis is selected as the plant material to be processed, the preferred oils to be volatilized may include the various chemical forms of cannabidiol (CBD), cannabidivarin (CBDV), delta-9-tetrahydrocannabinol (THC), delta-8-tetrahydrocannabinol, tetrahydrocannabivarin (THCV), cannabinol (CBN), cannabigerol, cannabichromene, chemically converted cannabinoids or any other cannabinoid. Other valuable terpenoid oils that may be extracted from cannabis may include the various chemical forms of linalool, caryophyllene, myrcene, limonene, humulene, pinene. By manipulating the temperature of the gas stream and/or heated surfaces that contact the plant materials within the volatilization chamber and completing successive extraction cycles, it is possible to isolate the various plant oils into substantially purified fractions. Alternatively, it is possible utilize a wider temperature band within the volatilization chamber to extract a range of plant oils in a single extraction cycle. As non-limiting examples, the following volatilization chamber temperatures may be utilized to extract various types of oils from cannabis: To target the extraction of delta-9-tetrahydrocannabinol, the temperature within the volatilization chamber should be kept near 315 degrees Fahrenheit. To target a mostly purified form of cannabidiol, the temperature should be kept near 315 degrees Fahrenheit in the first extraction cycle to first remove the delta-9-tetrahydrocannabinol from the plant material, and then the plant material should be processed a second time at a temperature near 356 degrees Fahrenheit to remove the remaining cannabidiol. To target extraction of both delta-9-tetrahydrocannabinol and cannabidiol in a single extraction cycle, the temperature within the volatilization chamber should be kept near 356 degrees Fahrenheit to volatilize both delta-9-tetrahydrocannabinol and cannabidiol in the same cycle. To target extraction of tetrahydrocannabivarin and all cannabinoids with a volatilization temperature below that of tetrahydrocannabivarin, the temperature of the volatilization chamber should be kept near 428 degrees Fahrenheit. Other combinations of different temperatures or successive extraction cycles may be used to target other oil compounds. Further discussion of temperatures and temperature ranges can be found in following sections of this disclosure.

Figure 9:
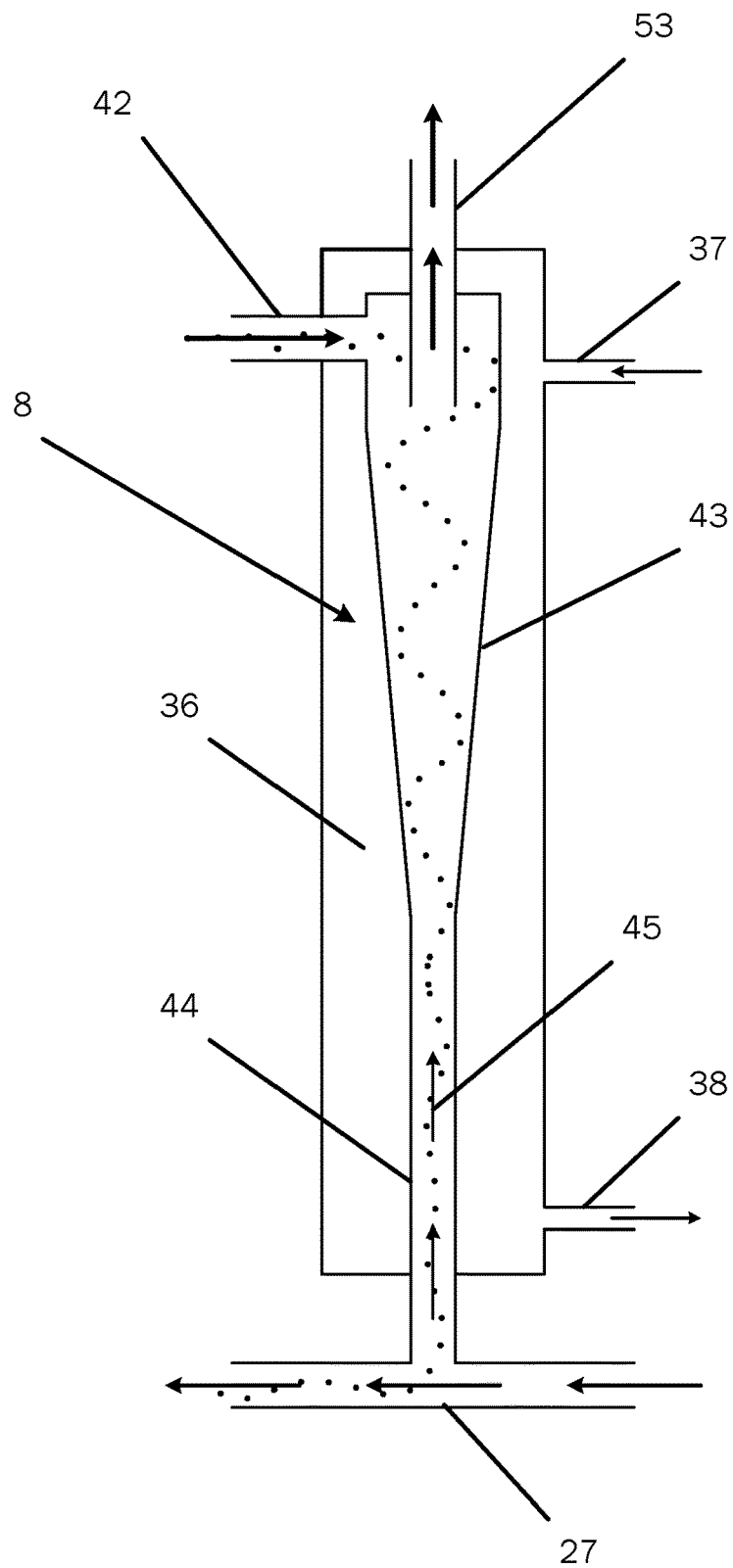
FIG. 9 is a detailed view of a primary plant material separation device and a secondary plant material entrainment section, for use with some embodiments.

After circulating within the volatilization chamber 7, the processed plant material and the volatilized plant oils may travel with the primary gas stream into a primary plant material separator 8. The oil may be referred to as an extracted oil. A detailed view of an embodiment of the primary plant material separator 8 is illustrated in FIG. 9 and will be discussed in greater detail in a following section of this disclosure. The processed plant material separator 8 is preferably a cyclone or centrifugal separator, however other centrifugal or non-centrifugal separation methods may be used to achieve the same or similar results. The primary plant material separator 8 separates the processed plant material from the primary gas stream containing the volatilized plant oils. The separated plant material exits through the bottom of the primary plant material separator, while the primary gas stream, along with the volatilized oils, exits through the top of the primary separator substantially free of entrained plant material. It should be noted that the positioning of the separated plant material exits and primary gas stream exits may be flipped or vary in placement depending on the differing requirements of the primary plant material separator design. Altering the placement of the exits should not be interpreted as being outside the scope of this invention.

Figure 2:
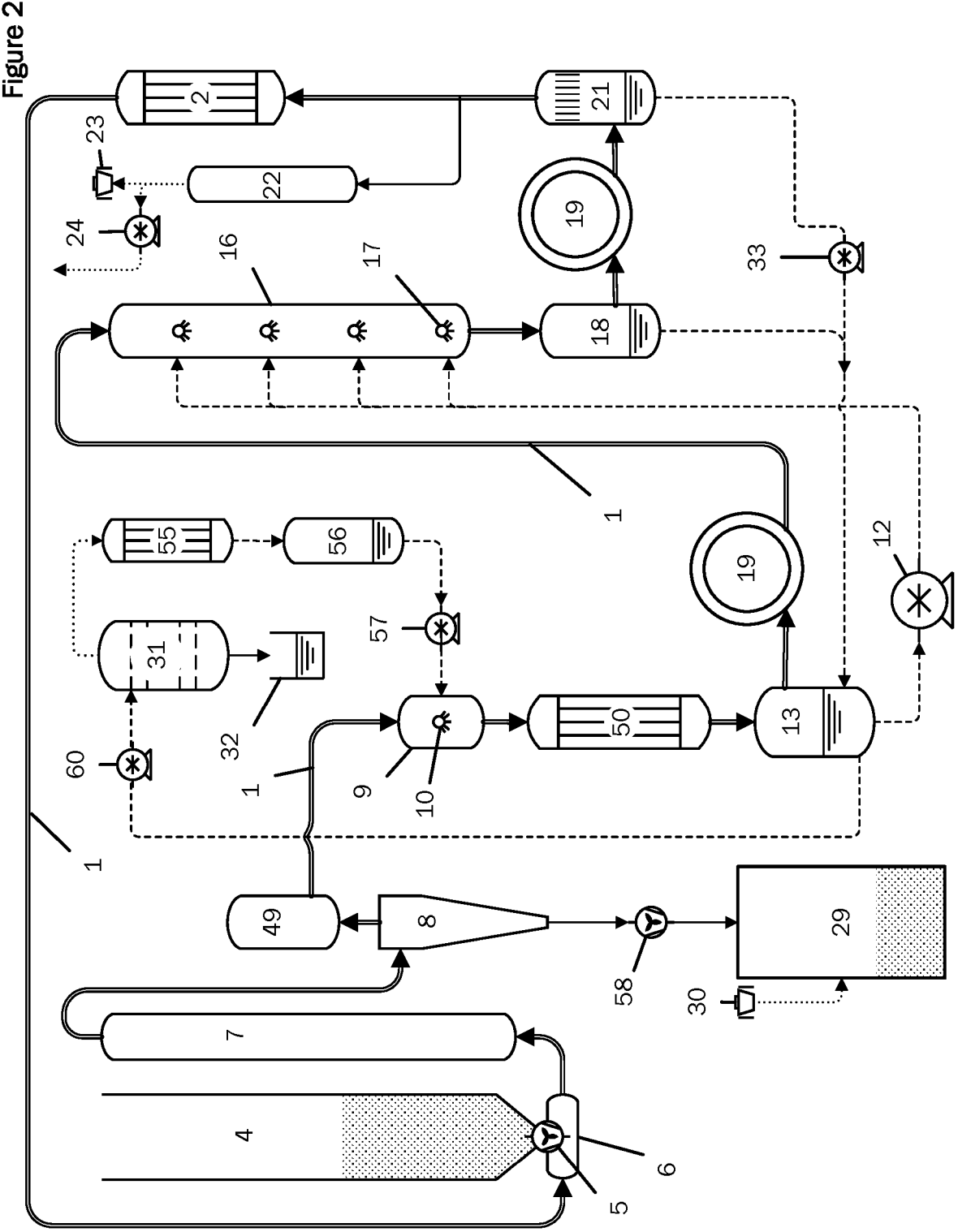
FIG. 2 is a diagrammatic view of an alternative embodiment of the present invention.

The separated processed plant material exiting the primary plant material separator 8 may optionally become entrained in a secondary gas stream 25 in a secondary entrainment zone 27, or may simply be in communication with a collection bin 29. The secondary gas stream 25 is propelled by a secondary gas stream mover 26, which is preferably a centrifugal blower. However, any other method of propelling the secondary gas stream may be used. The secondary gas stream is preferably kept at a lower temperature than the volatilization temperature of the plant oils in order to cool the processed plant material and prevent any continued volatilization or scorching from occurring. The processed plant material travels with the secondary gas stream into a secondary plant material separator 28. The secondary separator 28, which is preferably but not limited to a cyclone or centrifugal separator, separates the processed plant material from the secondary gas stream. However, any method capable of separating some or all of the processed plant material may be used. The processed plant material exits through the bottom of the secondary separator and is collected in a processed plant material collection bin 29. The secondary gas stream exits through the top of the secondary separator 28 substantially free of entrained plant material and continues to recirculate through the secondary gas stream loop 25. Other forms of plant material separation and collection may be used, such as the methods commonly employed in shop vacuum cleaners. Alternatively, a simple method of allowing the processed plant material to drop as a result of gravity or be mechanically propelled with an auger screw or other mechanical device from the bottom of the primary plant material separator 8 into a bin or disposal area may be used to avoid the need for a secondary gas stream 25 and the parts required for a secondary gas stream system. If such an alternative is used, it may be preferable in some applications to provide an airlock valve, flapper valve or other method of isolating the primary plant material separator from the outside atmosphere. One possible method of placing the primary plant material separator 8 is illustrated in FIG. 2, however, other methods may also be used.

The primary gas stream 1 and volatilized oils that exit the top of the primary separator 8 may optionally pass through a gas stream filter 49. The gas stream filter 49 is preferably designed to remove any or most of the remaining fine particulates from the gas stream that are not captured by the primary plant material separator. The gas stream filter 49 is preferably constructed of suitable materials to withstand the temperature of the heated gas stream. Such materials may include, but are not limited to, fiberglass filters or strainers, stainless steel or metal filters or strainers, sintered metal or glass filters, ceramic filters, or filters constructed of any other suitable materials.

After exiting the gas stream filter 49, the primary gas stream 1 and entrained volatilized oils travel into a cooling chamber 9, which may take the form of a cooling spray section 9, as shown. In embodiments that do not include a gas stream filter 49, the primary gas stream and entrained volatilized oils may travel into the cooling spray section 9 after exiting the primary plant material separator 8. Inside the cooling spray section 9, the primary gas stream 1 and entrained volatilized oils are contacted with a cooling spray 10 of a collection solvent that is emitted from one or more sprayers. The cooling spray 10 is supplied by a primary pump 12 that moves collection solvent to various sprayers and other areas throughout the system. As illustrated in FIG. 1, the primary pump 13 draws collection solvent from the sump area 13, however, in other embodiments, the primary pump 12 may draw collection solvent from other areas or other solvent reservoirs. In some embodiments, it is preferred that the cooling spray instead be supplied by a dedicated pump that draws from a reservoir or other source of substantially purified collection solvent. An example of such an embodiment is illustrated in FIG. 2 and a further description of such an embodiment is included in the sections of this disclosure that discuss the evaporation device 31.

The collection solvent may be optionally cooled by a collection solvent cooler 11. The collection solvent cooler 11 may be placed within the system such that it only cools the collection solvent before reaching the cooling spray section 9 or it may be placed before or after the primary pump 12 such that collection solvent spray traveling to any parts of the system are cooled. The collection solvent cooler 11 is preferably designed as liquid-cooled tube-in-shell heat exchanger or plate heat exchanger, however, air-cooled designs or any other suitable heat exchange device may be utilized. The collection solvent cooler 11 may be cooled by any type of fluid or gas. The cooling supply may be a liquid or gas that is pumped through an air-cooled or liquid-cooled heat exchange device, a municipal water supply or any other suitable method. It should be noted that, in some embodiments, providing sufficient cooling to the collection solvent system can provide cooling and temperature regulation of the entire system, in addition to that which is required to provide cooling to the cooling section 9. A further discussion of potential heat exchanger designs can be found in the sections of this document describing the gas stream cooler 50 and evaporation device 31 condenser. The designs and cooling methods used for the collection solvent cooler 11, gas stream cooler 50, the solvent recovery device 22 and evaporation device 31 condenser may be used interchangeably as needed for each cooler or condenser device to function as required in different embodiments and applications.

Upon being contacted with the cooling spray 10 within the cooling spray section 9, the primary gas stream is cooled and the volatized oils within the primary gas stream begins to condense. Preferably, the system and the flow rates of the gas stream and cooling spray solvent are designed such that a large portion of the volatilized oils condense directly on the surface of the cooling spray droplets, where they become directly captured in the collection solvent and drain directly or through other components of the system to reach the sump area 13 of the system. Much or all of the oils that do not condense on the droplets, condense within the gas stream into a fog of small and microscopic oil droplets, which travel out of the cooling section 9 entrained in the primary gas stream 1. While it is preferred to use a cooling spray 10 as a gas stream cooling and oil vapor condensation method, other methods may be used, including but not limited to contacting the primary gas stream with cooling coils, passing the primary gas stream through a tube-in-shell heat exchanger, or introducing a cooling gas directly into the primary gas stream. As such, element 10 may represent any of these components or more than one such component.

Upon exiting the cooling spray section 9, the primary gas stream may optionally pass through a gas stream cooler 50. The gas stream cooler 50 cools the gas stream, the entrained oil droplets and the mixture of collection solvent and captured plant oils preferably to a temperature that is sufficient to prevent heat degradation of the plant oils. The gas stream cooler 50 is preferably designed as a tube-in-shell heat exchanger that uses a flow of liquid or gas as a coolant medium. However, any air or liquid-cooled device may be used, including but not limited to exposing the gas stream to contact with vapor compression or absorption chiller coils. For liquid cooled designs, any coolant may be used, including but not limited to municipal water, water or various types of coolant fluids pumped or moved with the aid of a pump, vapor compression or absorption chiller coils or any other suitable method. The liquid coolant may be cooled using forced air, passive air, a vapor compression or absorption chiller, heat exchange with another liquid or any other suitable method. For air-cooled gas stream cooler designs, the gas stream cooler 50 may be cooled with forced air that is moved by the aid of an air mover, cool air from a vapor compression or absorption chiller, evaporative cooling from a swamp cooler or similar device or by passive contact with the surrounding atmosphere. It should be noted that providing sufficient cooling to the gas stream cooler 50 can provide cooling and temperature regulation of the entire system. It is preferred that the gas stream cooler be placed directly after a cooling spray 10 or collection solvent spray section such that the collection solvent washes any condensed oils from the gas stream cooler 50 and such that the time that the collection solvent and plant oils are exposed to heat is minimized, however, other placements may be used.

After exiting the optional gas stream cooler 50, the primary gas stream containing a fog of any entrained oil droplets that were not previously captured by the cooling spray, enters a sump section/liquid separator 13. In embodiments that do not include a gas stream cooler 50, the primary gas stream and entrained oil droplets may enter the sump section 13 after exiting the cooling spray section 9. The sump section 13 separates the majority of the liquefied collection solvent and extracted plant oil mixture from the primary gas stream and serves as a holding area for the collection solvent and captured extracted plant oil. In some applications, it may be desirable to incorporate a separate liquid separator (not shown) before the sump section 13 to facilitate separation of the collection solvent from the primary gas stream. Such a separate liquid separator could be as simple as a tee or bend in the gas stream path or may include demisting pads or other more advanced methods of separation. In some embodiments, a separate collection solvent reservoir (not shown) containing substantially purified collection solvent may also be included as a method to replenish any collection solvent that is lost or removed from the system as it operates.

After passing through the sump area 13, the primary gas stream and the fog of entrained oil droplets optionally enter an agglomeration section 14. The diameter of the agglomeration section 14 is preferably larger than that of the other passages within the primary gas stream loop 1 or is otherwise designed to be large enough to lower the velocity of the primary gas stream and maximize the time that the primary gas stream and the fog of oil droplets remain within the agglomeration section 14. It is also possible to use a longer agglomeration section, adjust the gas stream velocity, or use multiple agglomeration sections in parallel or in series to attain a similar result of maximizing the time that the oil droplets spend in the agglomeration section. Within the agglomeration section, the gas stream and fog of oil droplets are contacted with collection solvent vapor provided by collection solvent injectors 15. The collection solvent vapor 15 condenses on the surface of the cooler oil droplets, causing them to grow larger and increase in size and mass. Increasing the size and mass of the entrained oil droplets greatly enhances their removal from the gas stream in subsequent sections of the system. The preferred source of the collection solvent vapor is from the distilled collection solvent outlet of the evaporation device 31, however, other methods of providing collection solvent vapor may be used. Alternatively, mixing a cooler gas stream with a warmer gas stream as it enters the agglomeration section will achieve a similar result. Such an alternative method is described in PCT/IB2014/002383. Any collection solvent and other liquids that condense or coalesce on the surfaces within the agglomeration section 14 eventually drain down the agglomerator walls and into the sump area 13 of the system. Preferably, the diameter of the entrance of the agglomeration section and the passages leading from the sump area 13 to the agglomeration section 14 should be designed to be large enough to reduce the velocity of the primary gas stream such that condensing liquids can easily drain against the flow of the primary gas stream to reach the sump area 13. However, this may not be a requirement in some applications or with certain positionings of the agglomeration chamber within the system, such as when the gas stream enters through the top of the agglomeration section and exits through the bottom, for example.

After exiting the optional agglomeration section 14, the primary gas stream 1 and mist of enlarged oil droplets enter a collection chamber section 16. In embodiments that do not include an agglomeration section, the primary gas stream and entrained oil droplets may enter the collection chamber section 16 after leaving the sump section 13. In the collection chamber 16, the oil droplets entrained in the primary gas stream are bombarded with a high pressure spray 17 of collection solvent droplets emitted from one or more collection solvent sprayers 17. Any oil droplets that are impacted with collection solvent droplets 17 are effectively captured in the collection solvent, which collides with the walls of the collection chamber 16 and eventually drains to the sump area 13. Upon exiting the collection chamber, most of the larger oil droplets have been removed from the primary gas stream, although some of the smallest oil droplets may still remain. It should be noted that in some embodiments that do not include a dedicated cooling section or cooling spray section 9 or a dedicated collection chamber 16, the collection chamber section 16 could be considered to be the cooling section 9 and the cooling 9 section could be considered to be the collection chamber 16 section. In other words, the function of both the cooling spray section and the collection chamber section could be combined into one section in some embodiments of the system. In such embodiments where these sections are combined, it is preferred that the combined cooling spray/collection chamber section be located directly after the primary plant material separator 8 or directly after the gas stream filter 49, and in front of the gas stream cooler 50. However, other arrangements may be used. It should also be noted that in some embodiments the cooling section may be considered to be the gas stream cooler 50 or another cooling device or cooling area.

The primary gas stream optionally travels onward through a secondary liquid separation section 18. The secondary liquid separation section 18 separates the majority of the collection solvent from the primary gas stream to prevent the primary gas stream mover 19 from being overwhelmed by collection solvent. The secondary liquid separation section 18 may be as simple as a tee or bend in the gas stream passage or may include more advanced separation methods. The separated collection solvent drains from the liquid separation section 18 and back into the sump section 13 of the system. In some embodiments, the liquid separation section 18 may not be needed, depending on the ability of the primary gas stream mover 19 to handle entrained liquids. In other embodiments, it may be desirable to intentionally introduce some liquid into the gas stream mover 19 to facilitate cleaning and/or cooling of the gas stream mover 19.

The primary gas stream exiting the liquid separation section 18 enters the primary gas stream mover 19. In embodiments that do not include a liquid separation section 18, the primary gas stream enters the primary gas stream mover 19 after leaving the collection chamber 16. The primary gas stream mover 19 is preferably a regenerative blower, turbo blower, pressure blower or another type of blower that subjects the gas stream to a high level of centrifugal force, however, any method of propelling the primary gas stream may be used. Upon entering the primary gas stream mover 19, the primary gas stream is subjected to high centrifugal forces. Much or all of the remaining small and microscopic oil droplets and collection spray mist droplets that were not captured in preceding sections of the system impinge with the blades and housing of the primary gas stream mover 19. The oil and collection solvent droplets that impinge with the blades and housing of the gas stream mover 19 are effectively captured and removed from the primary gas stream. The captured oil and collection solvent drains from the exit of the primary gas stream mover or from a liquid drain port (not shown) within the gas stream mover, eventually reaching the sump section 13 of the system. In some embodiments, the gas stream mover may be utilized as the primary method of separating the entrained plant oil droplets from the gas stream. In such embodiments, it is preferable that the gas stream mover be supplied with a spray or stream of collection solvent to facilitate in washing the captured plant oils from the blower blades and housing. In such an embodiment, the gas stream mover or gas moving device may be considered part of the collection chamber and/or the gas moving device may form the only collection chamber for certain versions. The arrangement of the gas stream mover within the system may also be altered depending on the embodiment and application.

In some embodiments, the primary gas stream exiting the primary gas stream mover 19 travels into an optional droplet separator 20. This droplet separator 20 is preferably a cyclone or centrifugal separator, although other methods may be used. The droplet separator separates much or all of the remaining liquid droplets from the primary gas stream. The separated collection solvent and oil drains from the separator 20 into the sump area 13 of the system.

To prevent a portion of the primary gas stream from bypassing the main gas stream loop and traveling through the drainage tube of the optional droplet separator 20, and to otherwise prevent a pressure differential in the system from affecting drainage, an optional positive displacement/airlock pump 33 or similar device may be used to facilitate the drainage of the droplet separator 20 to the sump section 13 of the system. Such an airlock/pump 33 or similar device may also be used in embodiments that do not include an optional droplet separator 20 to facilitate drainage directly from the primary gas stream mover 19. An airlock/pump 33 or similar device may also be used for a similar function in embodiments that include the optional demister/polishing section 21 described in the following paragraph.

After exiting the droplet separator 20, the primary gas stream optionally enters a demister/polishing section 21. In embodiments that do not include a droplet separator 20, the primary gas stream may enter the demister/polishing section 21 after exiting the gas stream mover 19. The polishing section 21 polishes the primary gas stream and serves as a final droplet separation stage to remove much or all of the remaining collection solvent droplets prior to the primary gas stream passing through the primary gas heater. Providing effective droplet separation in the polishing section 21 and/or any preceding droplet separation sections prevents any droplets containing plant oils from coming in contact with the heated sections of the primary gas stream heater 2, thus preventing plant oils from burning, fouling or breaking down on the hot heater surfaces.

When the system is initially heated, the gases within the system will expand and may attempt to exit the system through any poorly sealed areas. Likewise, when the system is cooling, the gases within the system will contract. In order to prevent pressure or vacuum from building in the system, some embodiments provide a method of connecting the closed portion of the system to the atmosphere. Connection to the atmosphere is established through a solvent recovery device 22 such that as gases pass out of the system, any evaporated collection solvent is condensed and returned to the system. The solvent recovery device 22 is preferred to prevent collection solvent or volatilized plant oils from entering the surrounding atmosphere. The solvent recovery device 22 may utilize any known method of solvent recovery, including but not limited to a cold trap, a condensation tube, a filter, a distillation column, a commercially available solvent recovery system or any other suitable method. The solvent recovery device 22 may also contain a carbon filter or other type of odor capturing filter to prevent odors from escaping the system. Various condenser designs may be employed as the solvent recovery device 22, including any of the condenser designs discussed below in the paragraphs describing the evaporation device condenser 55.

An optional out-only check valve 23 is attached to the exit end of the solvent recovery device 22 to allow expanding gases to escape from the system when the system is heating and to prevent any atmospheric gases from traveling backwards into the system through the solvent recovery device 22 when the system is cooling. To allow atmospheric gases to enter the system when the system is cooling, an in-only check valve 30 may be connected to the processed plant material collection bin 29 or other places within the system.

Since the processed plant material will be removed from the system via the collection bin 29, it is desirable in some embodiments that collection solvent vapors be evacuated from this portion of the system to prevent their escape into the surrounding atmosphere. To keep this area evacuated of solvent vapors during times that the system is not cooling and thus naturally drawing gases in from the atmosphere, an evacuation pump 24 may be attached to the exit of the solvent recovery device 22. By continuously drawing a small amount of gas through the solvent recovery device 22 at all times, a small amount of vacuum is generated in the system, which draws fresh atmospheric gases into the processed plant material collection bin 29 via the in-only check valve 30, therefore displacing collection solvent vapors from the bin. An additional benefit of using an evacuation pump 24 in this manner is that the potential for solvent vapors escaping through any leaky seals within the system is mitigated. As an alternative to the evacuation pump, a displacing gas may be introduced to the processed plant material bin or any other areas within the system that are deemed desirable to displace. A preferred displacing gas would be CO2 or nitrogen, however, other displacing gases may be used. It should be known that utilizing an evacuation pump 24 or displacing gas is beneficial for multiple purposes (including preventing the condensation of volatilized oils at the plant material exit of the primary plant material separation device 8) and such use is not in any way dependent on a need to evacuate the processed plant material collection bin 29.

As will be discussed in a following section of this disclosure in greater detail when describing the primary plant material separator 8 and secondary plant material entrainment section 27 illustrated in FIG. 9, the evacuation pump 24 and/or addition of a displacing gas creates a slight backflow through the plant material separator 8 and serves an important function to prevent volatilized plant oils from escaping from the separated plant material exit 44 of the primary plant material separator 8 and condensing on the separated plant material exit 44 of the primary plant material separator 8 and/or the parts within the secondary gas flow loop 25 and/or processed plant material bin 29. If plant oils condense in these areas, it could cause plant material to stick to the internal surfaces of these parts and block the flow of separated plant material to the collection bin 29. While a passive method of evacuating plant oil vapors from these areas to prevent condensation is preferred, in some embodiments, it may be beneficial to include an auger screw or mechanical scraping method to ensure that these parts never become clogged.

In order to separate the captured plant oils from the collection solvent and plant oil mixture, some versions of the invention may optionally include an oil/solvent separation system such as an evaporation device 31. The evaporation device 31 is preferably, but not limited to, an evaporation device such as a thin film evaporator, wiped film evaporator, short path evaporator, rising film evaporator, falling film evaporator, spray dryer evaporator, centrifugal thin-film evaporator, or a conventional still design such as, but not limited to, stills that are commonly used to distill ethanol-based spirits. However, any suitable evaporation device may be used and one or more evaporation devices may be used alone or in combination for enhanced evaporation or multiple effect evaporation. Non-evaporative oil separation devices may alternatively be utilized. The evaporation device 31 may be operated at atmospheric pressure, under vacuum or above atmospheric pressure. Heat may be supplied to the evaporation device using electric heating elements, steam from a steam generator, a hot oil system, a thermal fluid, a heated gas or any other suitable method of supplying heat. In the case that the evaporation device is a thin film or wiped film evaporator, it is preferred that heat be supplied to the evaporator by wrapping the evaporation section with heat cables or by including a steam jacket or thermal fluid jacket around the evaporation section of the device and providing heat with a steam generator or thermal fluid system. In the case that the evaporation device is a rising film or falling film evaporator, it is preferred that heat be supplied to the falling or rising film section by a steam generator or thermal fluid system.

As the system is running, or in some embodiments, after the system has completed an extraction cycle, the evaporation device 31 draws a portioned flow of the mixture of collection solvent and captured plant oils from the sump area of the system by diverting some of the pressurized solvent from the primary pump 12 with the aid of a proportional valve, solenoid valve or other suitable diversion and/or portioning method (not shown) or with the aid of a dedicated feed pump 60 (shown in FIG. 2). Upon entering the evaporation device 31, the collection solvent is evaporated and distilled from the solvent and plant oil mixture and the solvent is reintroduced to the system as a substantially purified collection solvent. In the embodiment illustrated in FIG. 1, the purified collection solvent is reintroduced to the system as a vapor via collection solvent vapor injectors 15 in the agglomeration section 14 of the system. In this manner, the evaporated collection solvent vapors may be used to facilitate the function of the agglomeration section 14. The purified collection solvent may additionally or alternatively be introduced as a vapor to other sections of the system to aid in cleaning of the various components or serve other functions as required.

When the mixture of collection solvent and captured plant oils are introduced to the evaporation device, the plant oils, which preferably have a higher boiling point than the collection solvent utilized, do not readily evaporate within the evaporation device 31 and are concentrated into a substantially pure form as the collection solvent is distilled away. The concentrated plant oils exit the evaporation device 31 as a substantially pure extract which is subsequently collected in an extract collection area 32 as a final product of the system. Additional discussion of evaporation methods can be found in PCT/IB2014/002383, however, these methods should not be viewed as limiting. As an alternative to an evaporation device, other methods of separating the plant oils from the collection solvent may be used. In embodiments that use collection solvents that are immiscible with the plant oils being collected, stratification methods of separation may be employed. Chromatography methods may also be used to separate the oils from the collection solvent. Such methods serve as examples and are not limiting. Those of skill in the art will be able to determine the best separation method for different applications of the current invention.

FIG. 2 illustrates an additional embodiment of the present invention. In FIG. 2, the substantially purified collection solvent vapor exiting the evaporation device 31 passes through a condenser 55 to condense the collection solvent vapor into a liquid. The liquefied collection solvent exiting the condenser 55 flows into a purified solvent reservoir 56. A dedicated collection solvent pump 57 draws the substantially purified collection solvent from the purified solvent reservoir 56 and sprays the purified collection solvent directly into the cooling spray section 9 via the cooling spray 10. Alternatively, the purified solvent may be pumped directly from the condenser 55. Arranging the system in a manner whereby only substantially pure collection solvent is used in the cooling spray section 9, rather than recirculating collection solvent from the sump area 13, ensures that previously captured plant oils are not exposed to further heat by contacting the heated gas stream prior to it being cooled. In other applications and embodiments, it may be desirable to reintroduce the condensed collection solvent directly to the sump area 13 or any other area of the system where it is needed.

In embodiments of the invention where the evaporation device 31 includes a condenser 55, any condenser design may be used, including but not limited to liquid-cooled designs such as a Liebig, Allihn, Graham, Dimroth, Fridrichs or tube-in-shell condenser, or air cooled designs such as spiraled tubes, radiator style condensers or other designs that will be readily known to those of skill in the art. For liquid-cooled condenser designs, any coolant may be used, including but not limited to municipal water, water or various types of coolant fluids pumped or moved with the aid of a pump, vapor compression or absorption chiller coils or any other suitable method. The liquid coolant may be cooled using forced air, passive air, a vapor compression or absorption chiller, heat exchange with another liquid or any other suitable method. For air-cooled condenser designs, the condenser may be cooled with forced air that is moved by the aid of an air mover or by passive contact with the surrounding atmosphere. Such condenser designs and cooling methods may also be employed in the solvent recovery device 22, as mentioned above.

It is highly desirable to keep the internal surface temperatures of all portions of the system that contact the gas stream between the gas stream heater 2 and the first areas exposed to collection solvent or another cooling method near or above the condensation temperature of the volatilized plant oils. This is beneficial to prevent condensation of volatilized oils on undesired surfaces within the heated portions of the system, which could potentially damage the oils and/or hinder their recovery from the system. In order to maintain the temperature of the gas stream and to prevent condensation of volatilized oils on undesired surfaces within the heated portions of the system, in many embodiments of the invention it will be advantageous to house all or most of the heated portions of the system, including but not limited to all, some or any combination of the gas stream heater 2, the primary plant material separator 8, the primary plant material separator lower exit 44 (discussed in further detail in a following section), the optional gas stream filter 49 and the volatilization chamber/s 7, together in one passively insulated or actively heated box or heated chamber to simplify the insulating or heating of such components. Such a heated chamber may be passively insulated with a thermal insulation barrier such as fiberglass, ceramic wool, silica insulation, calcium silicate, aerogel, ceramic insulation, rock wool, mineral wool or any other suitable insulating medium. If the heated chamber is actively heated, electric elements may be used within the open space of the oven cavity with or without the aid of a convection fan, or a heated gas may be pumped through the oven chamber. Alternatively, the heated parts may be housed together in a vacuum chamber of suitable size for passive insulation, or a steam chamber of suitable size that may be supplied with steam as a heat source for active heating. The heated parts may also be wrapped with a heating cable. Finally, the heated parts may be contained in a chamber with a thermal heating liquid. Any heating or insulating method known to those of skill in the art may be utilized and still fall within the scope of this invention. It should be known that in most embodiments it may be important to construct the gas stream path such that the hopper section 4 is not housed within the oven chamber, yet is able to provide plant material to the entrainment zone 6. In embodiments wherein the heated components of the system are not contained within a heated box/oven chamber, or in embodiments wherein additional heating or insulation of the heated components is required, the heated components may be individually insulated or actively heated as discussed in the following sections of this document.

In some embodiments, a method of cooling the overall system must be used to prevent the system from overheating. Various methods of cooling the overall system using the collection solvent cooler 11 and/or the gas stream cooler 50 have been discussed in this disclosure. Additional methods, such as, but not limited to, circulating forced air or a cooling fluid over the external parts of the system may also be used. Passive methods of cooling the system, such as, but not limited to, including cooling fins or protrusions on various components of the system and gas stream loop may also be employed. It is also possible to house the system in a room or chamber of a regulated temperature. Further discussion of various additional cooling methods can be found in PCT/IB2014/002383.

Since the gas stream in most embodiments of the present invention will be saturated with collection solvent vapors in some areas, it is possible to promote an environment in the cool sections of the system that causes collection solvent vapors to condense on the internal surfaces of these sections. By causing collection solvent to condense on the internal surfaces of the cool sections of the system, the condensing collection solvent can be used to aid in washing these surfaces of any accumulated plant oils. To promote such a "condensation washing" environment, it is desirable to always keep the gas stream warmer than the internal surfaces of any areas of the system that contact the gas stream after the first cooled section of the system and before the gas stream heater section. Exceptions to this are the hopper section, the secondary gas stream 25 sections and separated plant material bin 29, where it is not desirable to have condensing collection solvent. The solvent that condenses on the internal surfaces of the cool sections of the system, along with any accumulated oils, drain through the system to eventually be collected in the sump area 13. Additional methods of "condensation washing" are described in PCT/IB2014/002383. Other methods may also be used.

The various valves, pumps, airlocks, electrical heaters and/or steam heaters, and any other controllable components of the system described in this disclosure may be regulated or controlled by mechanical methods and/or electronic temperature and/or pressure switches. It is, however, preferred that the temperatures and pressures within the system, the optional steam generator, evaporation device and various pumps, valves, airlocks, gas movers and other controllable components within the system be controlled by one or more programmable logic controllers (PLC control) and/or proportional integral derivative controllers (PID control) and/or other forms of computerized controls. Utilization of such electronic devices may achieve more precise control of the temperatures, pressures and various actions of the system. When electronic controls are implemented, the temperatures may be monitored by thermocouples, resistance temperature detectors (RTD sensors) and/or other temperature detection methods, the pressures may be monitored by electronic pressure sensors and/or mechanical pressure devices and/or other detection methods, the gas flow and liquid flow may be detected by electronic mass flow meters, pressure sensors, pressure differential sensors, Coriolis meters and/or other detection methods, the position of components may be detected with limit switches, position sensors, proximity sensors and/or other detection methods, the levels of fluids may be detected with optical, electrical, conductive, ultrasonic, capacitive, float switches and/or other detection methods and the levels of dry materials may be detected with optical, electrical, conductive, ultrasonic, capacitive, float switches, rotary dry level detectors and/or other detection methods. It may also be desirable to include sensors that can detect the saturation levels of water, plant oils or other liquids that have accumulated in the collection solvent mixture, such as capacitance sensors, conductivity sensors, specific gravity sensors, moisture sensors, refractometers or other types of sensors. Other sensors of various available designs may also be utilized as needed to measure the state of the various components and still fall within the scope of this invention. Non-limiting examples of how such thermocouples, sensors and devices that may be placed within the present invention can be found in PCT/IB2014/002383, which is incorporated in this application in its entirety by reference, however, the placement of sensors will be apparent to those who are skilled in the art. The various temperature, pressure, flow rate and other sensors may be placed within any section of the system, in any quantity and in any order and still fall within the scope of this invention. The various PLC, PID, computer or other control methods may regulate components within the system with various types of commercially available digital, analog and/or other types of input/output modules (IO modules), stepper controllers, variable frequency controllers, solid state relays, conventional magnetic relays and/or any other suitable method.

Figure 3:
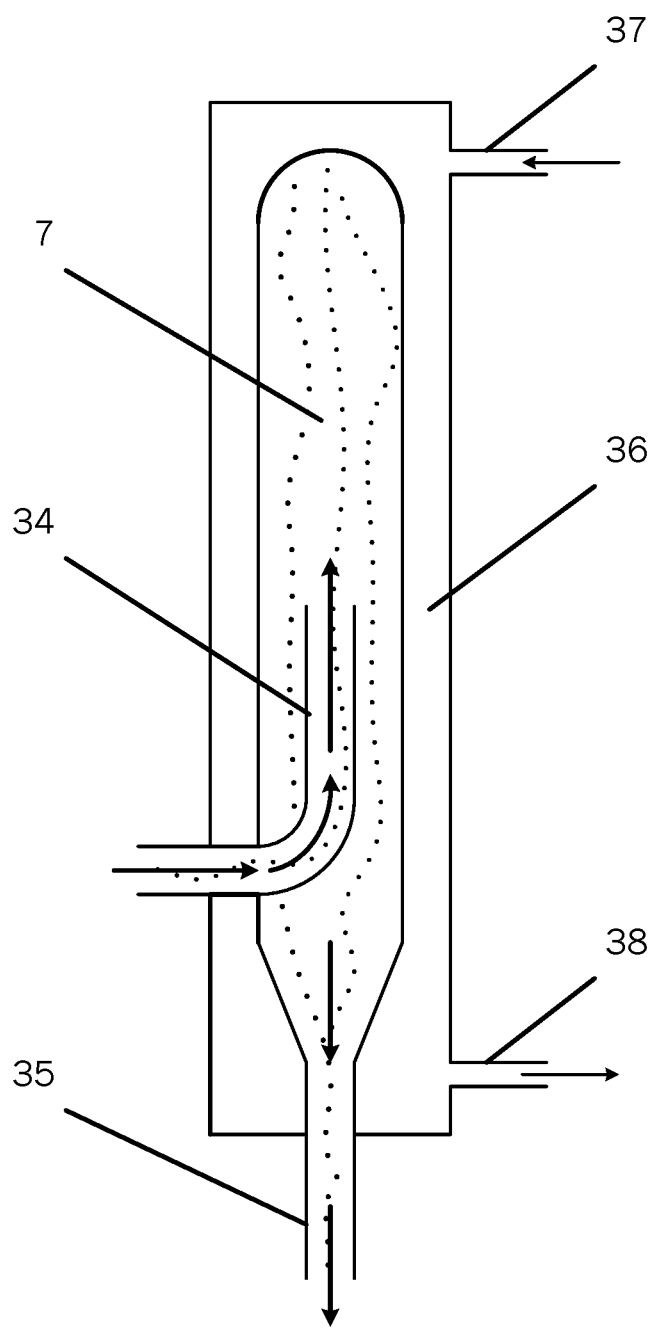
FIG. 3 illustrates an embodiment of a volatilization chamber designed to expose plant material entrained in the primary gas stream to a highly-turbulent and highly-agitatative environment to facilitate rapid volatilization of plant oils contained within the plant material.

FIG. 3 provides a detailed view of an embodiment of the volatilization chamber section of the system. The purpose of the volatilization chamber is to expose the plant material entrained in the primary gas stream to a turbulent and/or agitated environment to maximize contact with the gas stream and facilitate rapid volatilization of the plant oils contained within the plant material. This disclosure describes multiple methods to attain these results, including omission of the volatilization chamber in favor of a primary plant material separator with heated walls, however, other methods may be used to attain similar results and still fall within the scope of this invention. As illustrated in FIG. 3, the primary gas stream carries the entrained plant material into the volatilization chamber through an upward facing entry tube 34. Upon leaving the tip of the entry tube 34, which may include a high-velocity nozzle tip in some applications, the entrained plant material is blasted upward toward the top of the volatilization chamber 7. As the plant material travels upward, it is exposed to a turbulent reversal of the gas stream flow within the volatilization chamber. This action causes forceful agitation of the plant material and maximizes its contact with the heated primary gas stream to facilitate rapid volatilization of the plant oils contained within the plant material. The primary gas stream, along with the entrained plant material, exit the volatilization chamber through an exit passage 35 at the bottom of the chamber and travel onward to the primary plant material separator 8. One or more volatilization chambers of this type may be used in series or in parallel or in combination with other types of volatilization chambers. As such, element 7 in FIG. 1 and FIG. 2 may represent one or more volatilization chambers.

In order to maintain a sufficient temperature of the gas stream as it passes through the volatilization chamber and to prevent condensation of volatilized oils on surfaces within the volatilization chamber, it is preferred that most embodiments of the volatilization chamber discussed within this disclosure be contained or wrapped in a thermal insulation barrier and/or be provided with an active heat source. Such a heat source or thermal barrier may optionally be eliminated if the volatilization chamber/s are housed together with all or some of the other heated sections of the system within an insulated or heated chamber as discussed above. As a non-limiting example that may be applied to any of the embodiments of the volatilization chamber discussed or referred to in this disclosure, in FIG. 3, the volatilization chamber is illustrated housed within a heating jacket 36. To provide heat to the volatilization chamber 7, saturated steam of a specific pressure and temperature, a heated gas of a specific temperature or a heated thermal fluid of a specific temperature is pumped or otherwise introduced to the heating jacket through an entry passage 37. The steam and/or condensed steam, heated gas or thermal fluid circulates out of the heating jacket through an exit passage 38. In embodiments where steam is used as the heating medium, it is preferred, but not required, that the steam be supplied by the same steam generator that provides heat to the primary gas heater 2. Alternatively, an electrical heat source within the jacket space or an electrical heating wire wrapped directly around the volatilization chamber may also be used. Any of these methods may be used to heat any of the embodiments of the volatilization chamber discussed or otherwise referred to in this disclosure.

In some embodiments, it may be preferred to passively insulate the volatilization chamber with a thermal insulation barrier such as fiberglass, ceramic wool, silica insulation, calcium silicate, aerogel, ceramic insulation, rock wool, mineral wool or any other suitable insulating medium. It may also be preferred in some applications to house the volatilization chamber within a vacuum jacket. As a non-limiting example, such a vacuum jacket may look substantially similar to the heating jacket 36 illustrated in FIG. 3, except there would be no entry 37 or exit passages 38 for a heating medium. Instead, of heating medium entry and exit passages, an evacuation passage would be included that may include a check valve or similar vacuum containment method. Alternatively, the vacuum jacket may be permanently sealed or welded closed to retain the vacuum. Any of these methods may be used to insulate any of the embodiments of the volatilization chambers discussed or otherwise referred to in this disclosure.

Figure 4:
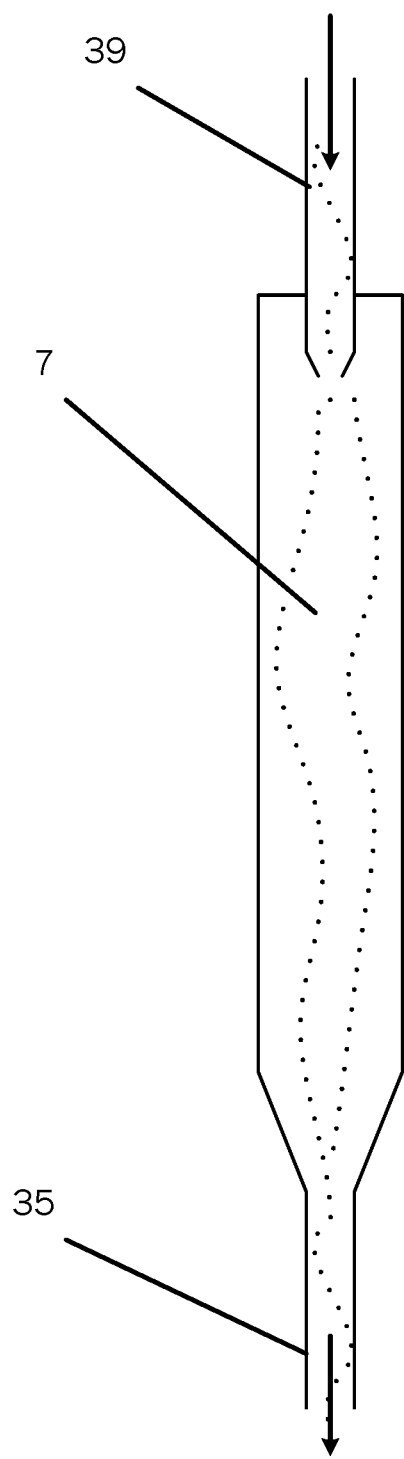
FIG. 4 illustrates an embodiment of the volatilization chamber that is also designed to expose the plant material entrained in the primary gas stream to a highly-turbulent and highly-agitatative environment to facilitate rapid volatilization of the plant oils contained within the plant material.
Figure 5:
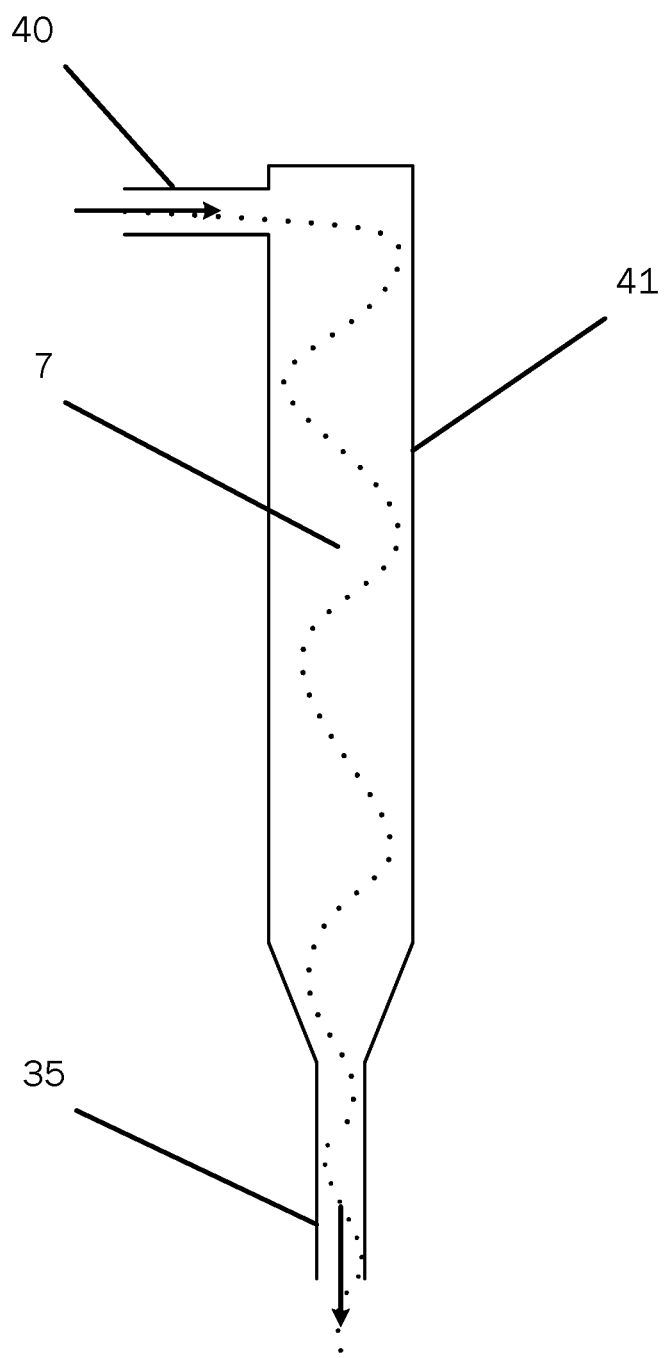
FIG. 5 illustrates an embodiment of the volatilization chamber that is designed to centrifugally force the plant material into contact with the heated walls of the volatilization chamber to induce rapid volatilization of the plant oils.
Figure 6:
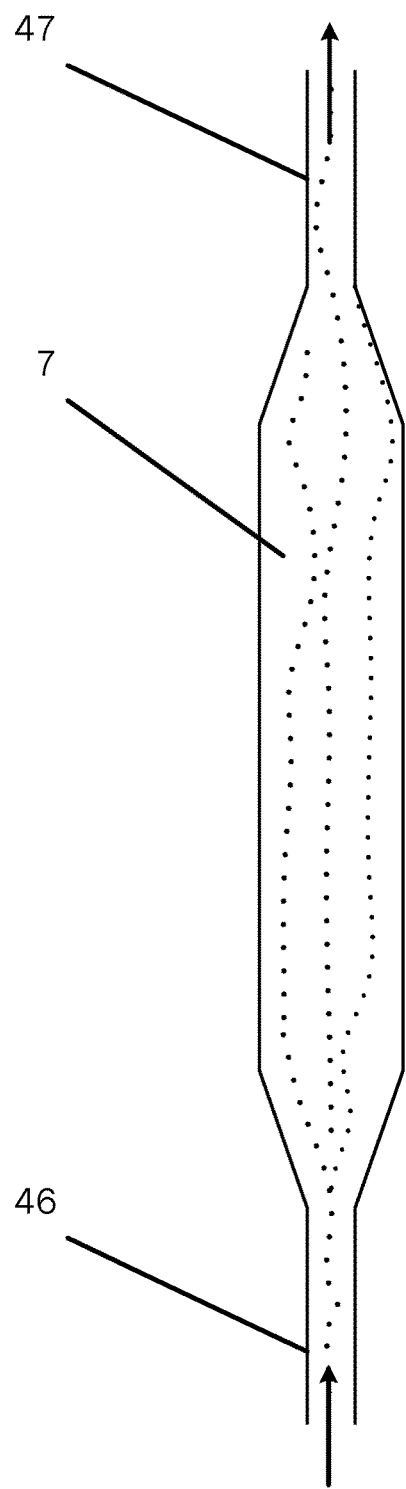
FIG. 6 illustrates an embodiment of the volatilization chamber that utilizes a modified form of pneumatic flash drying to induce rapid volatilization of oils within the plant material.

FIG. 4 illustrates an additional embodiment of the volatilization chamber section 7 of the system that utilizes a modified spray drying technique. Conventional industrial spray drying techniques typically involve spraying a mostly liquid feed that contains some solids into a heated gas stream as it enters a drying chamber. Those of skill in the art will be familiar with the design of such spray drying chambers. Within a conventional spray drying chamber, the liquids are evaporated and subsequently vented as waste, while the solids are collected as the final product. (An example of a conventional spray drying application where the liquid is vented and the solids are collected as the final product is the production of powdered milk.) In the current embodiment, the opposite final product is desired. Instead of the solids being desired, the liquid portion is desired as a final product. Therefore, the utilization of the spray drying technique is modified in this invention to handle a mostly dry feed instead of a mostly liquid feed. In the current invention, powdered or finely-ground plant material (a solid that contains liquid oils) is introduced into a heated gas stream that enters a drying chamber/volatilization chamber. This heated gas stream is the primary gas stream as defined in this invention. The primary gas stream carries the entrained plant material into the volatilization chamber 7 through a downward facing entry tube 39 with a nozzle tip. The primary gas stream and plant material rapidly exiting the nozzle facilitates a turbulent flow of the heated gas stream within the volatilization chamber and agitates the plant material to cause rapid volatilization of the oils contained within the plant material. The primary gas stream and entrained plant material exit the volatilization chamber through an exit passage 35 in the bottom of the chamber 7. One or more chambers of this type may be used in series or in parallel or in combination with any other types of volatilization chambers. Utilization of different nozzle designs, the addition of pressurized and/or hot air at the nozzle site, modifications to the dimensions and diameter of the spray drying chamber and other changes may benefit volatilization of the plant material and/or prevent plant material from sticking to the walls of the chamber in similar ways that such modifications benefit conventional spray drying techniques. In some embodiments, it may be advantageous to introduce the plant material directly at the nozzle site versus upstream of the nozzle in the entrainment area 6. Those of skill in the art will understand that many commercial spray drying techniques and designs may be adapted for use in the present invention. Such adaptations will still fall within the scope of the present invention. As with other embodiments of the volatilization chamber, in order to maintain the temperature of the gas stream and to prevent condensation of the volatilized oils on the surfaces within the volatilization chamber, it is preferred that the volatilization chamber be provided with its own heat source and/or a thermal insulation barrier. Examples of such heat sources and thermal barriers were discussed above, and may be applied to all embodiments of the vaporization chamber.

FIG. 5 illustrates a third embodiment of the volatilization chamber 7 that is designed to centrifugally force the plant material into contact with the heated walls of the volatilization chamber to induce rapid volatilization of the plant oils. One or more chambers of this type may be used in series or in parallel or in combination with other types of volatilization chambers. In the embodiment illustrated in FIG. 5, the primary gas stream 1 and the entrained plant material enter the volatilization chamber through a tangential entrance 40 at the upper end of the volatilization chamber 7. As the primary gas stream tangentially enters the volatilization chamber 7, the entrained plant materials are centrifugally forced into contact with the outer walls 41 of the chamber, where they spiral around the walls 41 of the volatilization chamber multiple times before eventually reaching the bottom exit 35 of the volatilization chamber. In order for successful volatilization of the plant oils to occur using this method, it is highly preferred that the walls 41 of the volatilization chamber be in contact with a heat source. However, in some applications the use of a thermal barrier may suffice. Examples of such heat sources and thermal barriers are discussed above, and may be applied to this embodiment and all other embodiments of the vaporization chamber.

FIG. 6 illustrates an embodiment of the volatilization chamber 7 that utilizes a modified form of pneumatic flash drying to induce rapid volatilization of oils within the plant material. One or more chambers of this type may be used in series or in parallel or in combination with other types of volatilization chambers. The primary gas stream containing entrained plant material enters the flash drying volatilization chamber 7 through a bottom entry passage 46 and carries the plant material upwards against gravity before exiting the chamber through an exit passage 47. The upper exit passage 47 may be relocated to the side of the chamber, however, it is preferred that the lower entry passage 46 remain at the lowermost point of the chamber 7. The diameter of the flash drying chamber and the flow rate of the primary gas stream must be carefully designed such that the heated gas flowing through the chamber is moving slightly faster than the natural freefall velocity of the plant material particles being processed. At this gas stream velocity, contact of the heated gas stream and plant particles is maximized, causing rapid volatilization of the plant oils. The length of the flash drying volatilization chamber 7 may be adjusted to maximize volatilization, or may be repeated with several shorter chambers arranged in series. As with other embodiments of the volatilization chamber, in order to maintain the temperature of the gas stream and to prevent condensation of the volatilized oils on the surfaces within the volatilization chamber, it is preferred that the volatilization chamber be provided with its own heat source and/or a thermal insulation barrier. Examples of such heat sources and thermal barriers are discussed above, and may be applied to all embodiments of the vaporization chamber.

Figure 7:
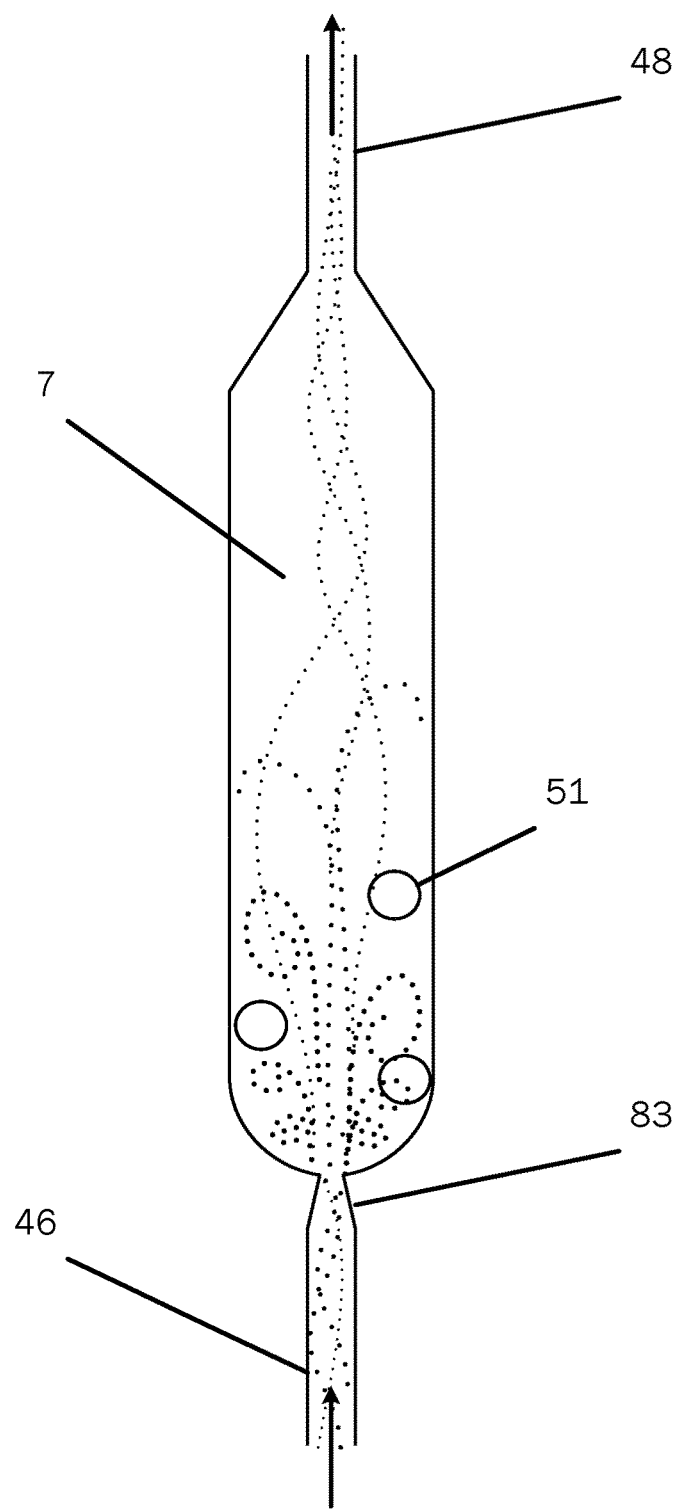
FIG. 7 illustrates an embodiment of the volatilization chamber that is designed to prevent plant material that is still heavily laden with oils or has clumped together from escaping the volatilization chamber until it has been broken up into small particles and fully stripped of its desirable oils.

FIG. 7 illustrates an additional embodiment of the volatilization chamber that is designed to prevent plant material that is still heavy laden with oils or has clumped into lumps from escaping the volatilization chamber until it has been broken up into small particles and has been fully stripped of its desirable oils. This special type of volatilization chamber is an adaptation of a flash drying chamber that is designed such that the diameter of the chamber and the gas stream flow volume create a gas velocity that only allows the smallest and most thoroughly oil-stripped particles of plant material, which are light enough to float upward in the gas stream, to exit the top of the chamber. Larger lumps or oil laden plant particles, which are too heavy to be carried up and out of the chamber, remain tumbling in an agitation zone until they are broken up and evaporated of their oils. It is only after the lumps of plant material are broken up and evaporated of their desirable oils that the plant materials become light enough and small enough to exit the chamber. As illustrated in FIG. 7, the gas stream carrying entrained plant material enters the volatilization chamber through a bottom passage 46. The diameter of the bottom passage is reduced to a small diameter before entering the chamber to form an air blade nozzle 47. The high velocity air from the nozzle 47 turbulently enters the volatilization chamber and helps forcefully break apart any lumps or chunks of plant material that are too heavy to travel upward in the chamber. The lighter and smaller particles of plant material are quickly stripped of their desired oils and continue to travel upward with the gas stream to exit the chamber through an exit passage 48. The heavier chunks of plant material cannot attain lift in the lower velocity gas stream areas of the chamber and remain near the bottom of the chamber where they continue to tumble and impact one another and the walls of the chamber while simultaneously getting dryer as the oils that they contain volatilize in the heated chamber at a slower rate. Together, this effect of tumbling and drying causes the plant material lumps to break apart into progressively finer and finer particles. Once the particles are fine and light enough, they can attain the lift that they need to be carried by the rising gas stream to exit the top of the chamber through the exit passage 48. Other embodiments of this unique volatilization chamber design may include hollow or solid balls or beads or other objects of other shapes constructed of stainless steel, other metals, ceramics, thermal plastics, or any other suitable material to aid in breaking up the plant material. A non-limiting example of such an element is represented by a ball 51 in FIG. 7. In such embodiments, the balls or other milling objects will be thrown around within the chamber by the air nozzle 83 to facilitate breaking up of the plant material. An excluder screen or other exclusion method may optionally be included to prevent a stray ball or milling object from escaping the volatilization chamber. Alternatively, the fast moving gas stream entering the chamber may be used to power a turbine blade (not shown) to a high velocity. The optional high velocity turbine blade may be used to break up any large particles of plant material moving around the bottom sections of the chamber. Such a blade could also be rotated by an externally powered shaft that passes through a wall of the chamber or incoming gas passage, or by a magnetic coupling to avoid the need for a shaft seal and/or shaft penetration hole that could potentially leak. The blade and milling object designs used in this embodiment of the vaporization chamber could be adapted for use in any of the vaporization chamber embodiments discussed in this disclosure. While the volatilization chamber illustrated in FIG. 7 is illustrated as having a concave bottom area, in other embodiments it may be desirable to utilize a conical bottom area to continuously funnel the falling heavier plant materials back into the air pick or blade area. As with other embodiments of the volatilization chamber, in order to maintain the temperature of the gas stream and to prevent condensation of the volatilized oils on the surfaces within the volatilization chamber, it is preferred that the volatilization chamber be provided with its own heat source and/or a thermal insulation barrier. Examples of such heat sources and thermal barriers are discussed above, and may be applied to all embodiments of the vaporization chamber.

Figure 8A:
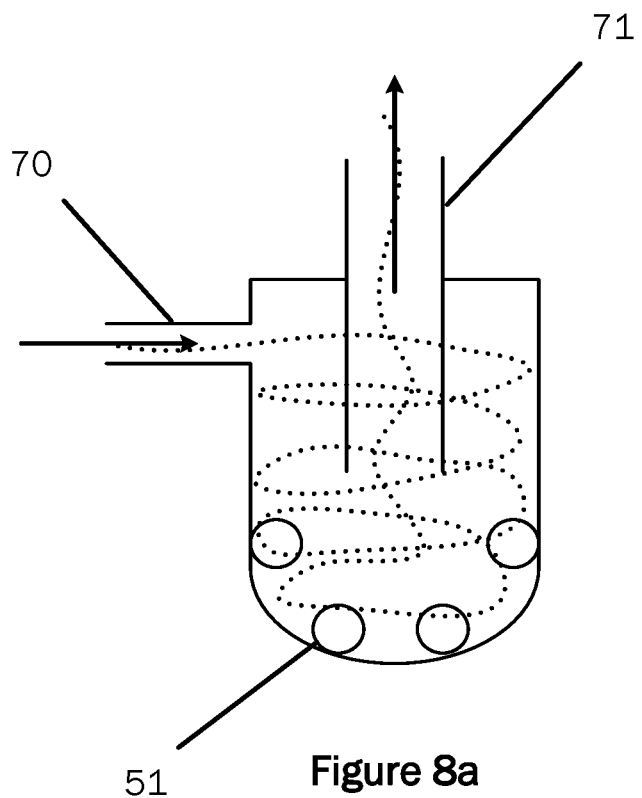
FIGS. 8a and 8b illustrate a cross-sectional and a top view of an additional embodiment of the volatilization chamber that is designed to prevent plant material that is still heavily laden with oils or has clumped together from escaping the volatilization chamber until it has been broken up into small particles and fully stripped of its desirable oils.
Figure 8B:
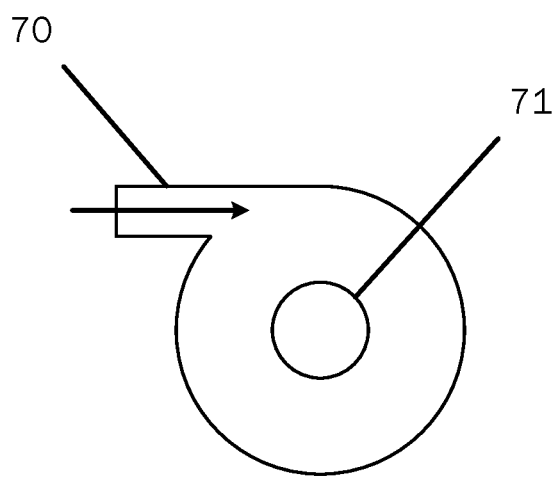

FIGS. 8*a* and 8*b* illustrate a cross-sectional and a top view of another embodiment of the volatilization chamber that is designed to prevent plant material that is still heavy laden with oils or has clumped into lumps from escaping the volatilization chamber until it has been broken up into small particles and been fully stripped of its desirable oils. In this embodiment, the gas stream and entrained plant material enters the volatilization chamber through a tangential side entrance 70. The gas stream enters at a high velocity and causes the entrained plant materials to spiral rapidly within the volatilization chamber. Optionally, hollow or solid balls or beads or other milling objects of other shapes constructed of stainless steel, other metals, ceramics, thermal plastics, or any other suitable material may be included in the volatilization chamber to aid in breaking up the plant material. These milling objects are preferably sized such that they cannot exit the chamber and continue to rapidly spiral along the walls of the chamber, grinding and breaking up any large plant material particles. Optionally, an excluder screen or other exclusion device may be used to prevent any chance of the milling objects from exiting the chamber. A non-limiting example of a few hollow milling balls 51 are illustrated in FIG. 8*a*. The exit of the volatilization chamber is designed and positioned such to serve as a particle classifier that allows only the smallest and lightest particles of plant material to leave the chamber. In this way, only the plant materials that have been thoroughly broken up and have been substantially stripped of their desired oils can exit the chamber, where the heavier plant materials that still contain oils will continue to circulate within the volatilization chamber until they are light enough to leave. The embodiment of the volatilization chamber illustrated in FIGS. 8*a* and 8*b* functions in a similar way to a cyclone separator in that it centrifugally excludes larger particles from leaving through the primary chamber exit 71. However, it is very different from a typical cyclone separator in that it does not have a secondary exit for captured particles to escape and that eventually all of the plant material particles do escape through the primary exit. Instead of permanently separating the plant particles from the gas stream like a conventional cyclone, the plant material particles continue to circulate within the volatilization chamber until they are stripped of enough of their oils and are ground to a fine dust. When the plant material particles have attained a low enough mass to no longer be affected by centrifugal separation, they are carried out the main exit by the gas stream and eventually are separated by the primary plant material separator. By delaying the departure of the plant materials from the volatilization chamber in such a way, nearly complete extraction of the plant oils may be attained. The embodiment of the volatilization chamber illustrated in FIGS. 8*a* and 8*b* may be used in parallel or in series with additional similar volatilization chambers or in combination with any of the other volatilization chambers described in this disclosure. In particular, it may be beneficial to use this embodiment of the volatilization chamber before a flash drying chamber such as the embodiment illustrated in FIG. 6.

While not illustrated in any figures in this disclosure, another embodiment of the volatilization chamber that may be preferred with some types of plant materials would consist of a pneumatic ring dryer design. The term pneumatic ring dryer is well defined in industrial drying literature and the design of a ring dryer will be well known to those of skill in the art. A ring dryer version of the volatilization chamber will have the benefit of allowing plant material to graduate through the system only after the desirable oils have been volatilized. Other methods that may attain excellent volatilization of the plant oils may include spin flash drying systems, spin flash drying systems with agitator blades, rotating drum dryers, ball mill dryers, dryers with particle classifiers and other methods that will be known to those of skill in the art.

FIG. 9 illustrates a detailed view of an embodiment of the primary plant material separation device 8 and the secondary plant material entrainment section 27. As illustrated in FIG. 9, the primary separation device is a cyclone separator. However, other centrifugal or non-centrifugal separation methods may be used. The primary gas stream and entrained plant materials enter the primary plant material separation device through a tangential entrance 42 at the side of the separator 8. Upon entering the primary plant material separator, the entrained plant materials are centrifugally forced into contact with the outer walls 43 of the separator 8, where they spiral down the walls 43 of the separator and fall from the bottom exit of the separator and eventually reach the processed plant material collection bin 29. The primary gas flow exits through the top portion 53 of the separator substantially free of entrained plant material and continues to the optional gas stream filter 49 or directly to the cooling spray section 9 of the system. While many centrifugal separators are oriented in the position described in FIG. 7, it will be known to those of skill in the art that the orientation of the separator may be altered and that a repositioning of the top and/or bottom exits and/or side entry points (if applicable) will still fall under the scope of the present invention.

It should be noted that one or more primary plant material separation devices may be used in parallel or in series or both in parallel and in series to obtain more complete separation of the entrained plant materials from the primary gas stream. In the case that a cyclone separator is used as the primary plant material separation device, better separation can be achieved by the utilization of several small cyclones in parallel, each of a smaller diameter with a lower volume of gas flow, versus using one cyclone of a large diameter with a higher volume of gas flow. Placing cyclones in series also achieves better separation. In the interest of maintaining simplicity in the design of the invention, it is preferable to use the least amount of cyclones required to achieve the desired level of separation. This applies not only to the primary separation cyclone, but also to any other plant material or droplet separation cyclones used within the system.

As illustrated in the embodiment of the primary plant material separator 8 that is depicted in FIG. 9, as the separated plant material falls from the bottom exit of the separator 8, it optionally passes through a specialized, heated and/or insulated exit tube 44. This heated exit tube 44 is also illustrated in the flow diagrams in FIG. 1. Upon reaching the bottom of the heated exit tube 44, the processed plant material falls into the secondary entrainment section 27 where it is entrained in the secondary gas stream 25 and propelled into the secondary plant material separator 28 to eventually fall into the processed plant material collection bin 29. It is preferable that the secondary gas stream 25 be maintained at a lower temperature than the primary gas stream 1, such that the processed plant material is cooled upon coming in contact with the secondary gas stream 25. By cooling the processed plant material, further volatilization is arrested and heat degradation of the plant material is prevented. This is especially important in the case that the operator of the system desires to perform a second, higher temperature extraction of the plant material to extract plant oils of a higher boiling point than those that were extracted in the first extraction cycle. Failure to cool the processed plant material could damage the remaining oils and could also lead to degraded oil vapors traveling upwards from the collection bin and into the primary gas stream as the system operates, thereby reducing the quality of the extract. As an alternative, a simple method of allowing the processed plant material to drop as a result of gravity or be mechanically propelled from the bottom of the primary plant material separator 8 into a bin or disposal area may be used to avoid the need for a secondary gas stream 25 and the parts required for a secondary gas stream system. If such an alternative is used, it may be preferable in some applications to provide an airlock valve, flapper valve or other method of isolating the primary plant material separator from the outside atmosphere.

As processed plant material travels down the heated exit tube 44, a portioned, small volume of atmospheric gas or displacing gas is simultaneously entering the system through the in-only check valve 30 connected to the processed plant material collection bin 29 and subsequently mixing with the gases in the secondary gas stream 25. This gradual inward flow of the atmospheric or displacing gas slowly flows up into the system through the same heated tube 44 that the processed plant material is falling down, against the downward flow of falling plant material. This flow of atmospheric gas or displacing gas (illustrated by the small, upward traveling arrows 45 in the heated exit tube 44) serves an important purpose—it prevents plant oil vapors from escaping from the exit of the primary plant material separator 8 and condensing on the parts within the secondary gas flow loop 25 and processed plant material bin 29. To prevent any condensation from occurring within the lower exit portion of the primary plant material separator 8, the heated exit tube 44 should be of sufficient length such that the vapor-free atmospheric or displacing gas is heated to near or greater than the volatilization temperature of the plant oils being volatilized prior to reaching the bottom portion of the primary plant material separator 8. The heat source for the heated exit tube 44 may be the heating jacket 36 described in the following paragraph, or a separate heating jacket that is heated by a similar method to the heating jacket 36 described in the following paragraph. Alternatively, the heated exit tube 44 may be directly wrapped in an electric heating cable or similar device. The displacing gas may also be heated by other methods. One non-limiting example would be to place a spiraled atmospheric gas or displacing gas tube constructed of a metal, silicone or other heat resistant material in a heated area of the system or within the heated chamber that houses some or all of the heated components in some embodiments, such that the displacing gas is heated prior to being introduced to the separated plant material exit tube 44. Another non-limiting example would be to wrap a displacing gas or atmospheric displacing gas tube of suitable material in heating coils. Other methods may also be used to heat the gas being introduced to the separated plant material exit 44. In cases where the method of displacing volatilized plant oils from the separated plant materials exit 44 are not effective or not deemed to be the best option, mechanical methods of removing accumulated plant oils from the plant material exit 44 and pathways to the separated plant material bin 29 may be employed. A few non-limiting examples include utilization of an auger screw or auger conveyor, rotating scraper blades, plunger pistons, a belt system or other methods that will be known to those of skill in the art.

It should be noted that supplying the walls 43 of the primary plant material separator 8 with a sufficient heat source may be desirable and may have the added benefit of providing an option to omit the preceding volatilization chamber section 7 of the system in some circumstances. If sufficient heat can be transferred to the plant material through direct contact with the heated walls 43 of the primary plant material separator 8, sufficient volatilization and extraction will occur without the need for a separate volatilization chamber 7. As illustrated in FIG. 9, both the processed plant material exit tube 44 and the primary plant material separator 8 are housed within a heating jacket 36. To provide heat to the plant material separator 8 and plant material exit tube 44, saturated steam of a specific pressure and temperature, a heated gas of a specific temperature or a heated thermal fluid of a specific temperature is pumped or otherwise introduced to the heating jacket through an entry passage 37. The steam and/or condensed steam, heated gas or thermal fluid circulates out of the heating jacket through an exit passage 38. In embodiments where steam is used as the heating medium, it is preferred, but not required, that the steam be supplied by the same steam generator that provides heat to the primary gas heater. Alternatively, an electrical heat source within the jacket space or an electrical heating wire wrapped directly around the plant material separator 8 and/or exit tube may also be used.

As with the previously described volatilization chamber embodiments, in some embodiments of the primary plant material separator, it may be preferred to passively insulate the primary plant material separator 8 with a thermal insulation barrier such as fiberglass, ceramic wool, silica insulation, calcium silicate, aerogel, ceramic insulation, rock wool, mineral wool or any other suitable insulating medium. It may also be preferred in some applications to house the primary plant material separator 8 within a vacuum jacket. By way of example only, such a vacuum jacket would look substantially similar to the heating jacket 36 illustrated in FIG. 9, except there would be no entry 37 or exit passages 38 for a heating medium. Instead, an evacuation passage would be included that may include a check valve or similar vacuum containment method. Alternatively, the vacuum jacket may be permanently sealed or welded closed to retain the vacuum. The primary plant material separator and/or separated plant material exit tube 44 may also be housed within an insulated and/or heated chamber with all or some of the heated components of the system. Such a method has been described in detail in other sections of this disclosure.

Figure 10:
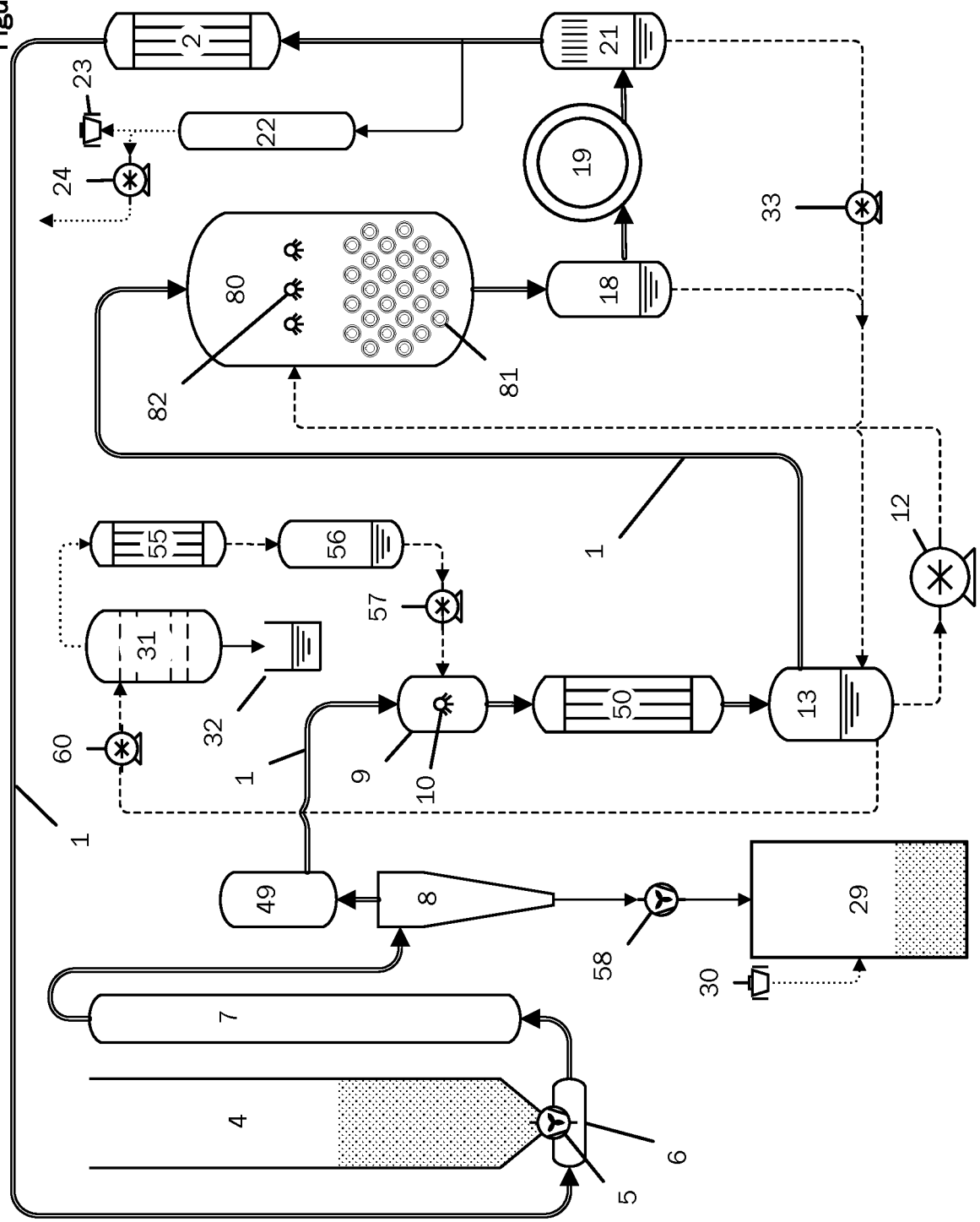
FIG. 10 illustrates an embodiment that utilizes a collection chamber containing wetted packing.

In some cases, more efficient collection of the volatilized plant oils may occur through the utilization of a wetted packing material 81. Non-limiting examples of embodiments that utilize wetted packing materials are discussed in PCT/IB2014/002383, which is incorporated herein in its entirety, by reference. One example of a collection chamber containing wetted packing is illustrated in FIG. 10. Such an embodiment utilizing wetted packing may include a collection chamber 80 containing a wetted substrate 81 such as, but not limited to, random packing including raschig rings, saddles and beads made of glass, ceramics metals or other materials, other random packing materials such as sand, alumina, gravel, PTFE fibers, stainless steel wool, fiberglass or mineral wool fibers, and structured packing such as knitted packing, woven wire mesh, stainless steel wool, stainless steel matting, woven stainless steel mesh, corrugated metal sections, bubble-cap plates and sieve tray plates or other types of packing to capture the volatilized plant oils. The packing material 81 may be wetted with collection solvent, which may collect the plant oils and eventually drip down through the packing material to the sump area 13 to be recovered. In FIG. 10, the packing material may be wetted by collection solvent sprayers 82 or by other methods of contacting the packing material with collection solvent. As with other embodiments, it should be known that the wetted packing collection chamber 80 illustrated in FIG. 10 may also serve as the system's cooling chamber, with the sprayers 82 and/or packing material 81 serving to cool the gas stream. Alternatively, a separate cooling chamber may be provided upstream of the collection chamber 80, as is already illustrated in FIG. 10. A collection chamber with a wetted packing material may be used in other embodiments and in combination with collection chambers with collection solvent sprayers 17 or any other collection methods. The location of the collection chamber 80 may also be varied depending on the application. As one non-limiting example, the wetted packing collection chamber 80 may be relocated to the position of the gas stream cooler 50.

Finally, it should be known that in addition to the oil droplet collection methods previously discussed, an electrostatic method of capturing condensed oil droplets may also be employed in the present invention. In such embodiments, an electrostatic scrubber, the design of which will be readily known to those who are skilled in the art, may be placed after the cooling section 9 of the system. With this placement, the electrostatic collection plates may be optionally washed of collected oils by the falling collection solvent. The electrostatic collection plates may also be placed after the agglomeration section 14 or after the collection chamber section 16 and may be optionally washed with a spray of collection solvent. If efficient electrostatic collection occurs, it may be possible to reduce or eliminate some of the other collection methods throughout the system.

By way of non-limiting example only, the following operating conditions and delivery rates may be utilized to extract plant oil: A centrifugal-type gas stream mover 19 capable of providing an outlet pressure of approximately 1.0 to 5.0 pounds per square inch is utilized to move the gas stream 1 throughout the system. Other examples may include a gas stream mover capable of providing an outlet pressure of 0 to 150 pounds per square inch. The gas stream mover 19 moves the gas stream 1 throughout the system at a flow rate of approximately 30 to 100 standard cubic feet per minute. Other examples may include a gas stream mover capable of providing a flow rate of approximately 0.1 to 30 standard cubic feet per minute, 100 to 200 standard cubic feet per minute, 200 to 500 standard cubic feet per minute, over 500 cubic feet per minute or other ranges. As the gas stream passes through the gas stream heater 2, the gas stream is heated to a temperature of approximately 290 to 430 degrees Fahrenheit. In other examples, the gas stream may be heated to a temperature range of approximately 100 to 300 degrees Fahrenheit, 100 to 310 degrees Fahrenheit, 200 to 300 degrees Fahrenheit, 200 to 310 degrees Fahrenheit, 280 to 450 degrees Fahrenheit, 300 to 500 degrees Fahrenheit, 300 to 400 degrees Fahrenheit, 300 to 370 degrees Fahrenheit, 300 to 365 degrees Fahrenheit, 305 to 360 degrees Fahrenheit, 300 to 360 degrees Fahrenheit, 300 to 330 degrees Fahrenheit, 310 to 320 degrees Fahrenheit, 340 to 370 degrees Fahrenheit, 350 to 360 degrees Fahrenheit, 350 to 365 degrees Fahrenheit, 415 to 445 degrees Fahrenheit, any combination of these temperature ranges or other temperature ranges. Powdered or finely-ground plant material containing plant oils is fed into the gas stream 1 via an entrainment zone 6 at a rate of approximately 0.03 to 0.25 pounds per minute. Other examples may include a feed rate of 0.001 to 0.03 pounds per minute, 0.25 to 1.0 pounds per minute, 1.0 to 5.0 pounds per minute, 5.0 to 10.0 pounds per minute, more than 10.0 pounds per minute or other feed rates. To the greatest degree possible, the internal surface temperature of the extraction chamber 7 area and all areas of the system that contact the gas stream as the gas stream passes between the gas stream heater 2 and the gas stream cooling section 9 are kept above the condensation temperature of the volatilized oils or near the temperature of the gas stream exiting the heater 2 to prevent condensation of plant oils on these surfaces. In some examples, this temperature is kept near or above approximately 290 to 430 degrees Fahrenheit. In other examples, the temperature may be kept in a range of approximately 100 to 300 degrees Fahrenheit, 100 to 310 degrees Fahrenheit, 200 to 300 degrees Fahrenheit, 200 to 310 degrees Fahrenheit, 280 to 450 degrees Fahrenheit, 300 to 500 degrees Fahrenheit, 300 to 400 degrees Fahrenheit, 300 to 370 degrees Fahrenheit, 300 to 365 degrees Fahrenheit, 305 to 360 degrees Fahrenheit, 300 to 360 degrees Fahrenheit, 300 to 330 degrees Fahrenheit, 310 to 320 degrees Fahrenheit, 340 to 370 degrees Fahrenheit, 350 to 360 degrees Fahrenheit, 350 to 365 degrees Fahrenheit, 415 to 445 degrees Fahrenheit, any combination of these temperature ranges or other temperature ranges. The evaporation device 31 is operable to distill approximately 0.04 to 0.15 gallons per minute of collection solvent from the mixture of plant oils and collection solvent. Other examples may include separation rates of approximately 0.0002 to 0.04 gallons per minute, 0.15 to 0.5 gallons per minute, 0.5 to 1.0 gallons per minute, 1.0 to 5.0 gallons per minute, 5.0 to 10.0 gallons per minute, more than 10.0 gallons per minute or other rates. The distilled collection solvent is stored in a separate reservoir 56 from the sump reservoir area 13. A substantially purified flow of collection solvent is pumped to the cooling spray 10 at a rate of approximately 0.03 to 1.0 gallons per minute. Other examples may include rates of 0.0002 to 0.03 gallons per minute, 1.0 to 7.0 gallons per minute, 7.0 to 10.0 gallons per minute, greater than 10.0 gallons per minute, less than 10.0 gallons per minute or other rates. The cooling spray cools the gas stream to approximately 160 to 180 degrees Fahrenheit. In other examples, the cooling spray cools the gas stream to approximately 80 to 150 degrees Fahrenheit, 0 to 150 degrees Fahrenheit, 0 to 100 degrees Fahrenheit, 40 to 80 degrees Fahrenheit, less than 180 degrees Fahrenheit, less than 173 degrees Fahrenheit, less than 150 degrees Fahrenheit, less than 140 degrees Fahrenheit, less than 130 degrees Fahrenheit, less than 120 degrees Fahrenheit, less than 110 degrees Fahrenheit, less than 100 degrees Fahrenheit or other temperatures. After contacting the cooling spray, the gas stream and entrained liquids pass through the primary gas stream cooler 50. The gas stream cooler 50 cools the gas stream and entrained liquids/oils to approximately 90 to 150 degrees Fahrenheit. In other examples, the gas stream cooler cools the gas stream and entrained liquids/oils to approximately 0 to 150 degrees Fahrenheit, 0 to 100 degrees Fahrenheit, 40 to 80 degrees, 0 to 90 degrees Fahrenheit, less than 150 degrees Fahrenheit, less than 140 degrees Fahrenheit, less than 130 degrees Fahrenheit, less than 120 degrees Fahrenheit, less than 110 degrees Fahrenheit, less than 100 degrees Fahrenheit, less than 90 degrees Fahrenheit, less than 80 degrees Fahrenheit, or other temperatures. In embodiments using only a spray cooler or a spray collection chamber to cool the gas stream, these sections may be operable to cool the gas stream and entrained liquids/oils to approximately 90 to 150 degrees Fahrenheit or any of the temperature ranges listed above for the cooling spray or gas stream cooler. In embodiments in which the collection solvent is cooled by a cooler, such as 55, before being sprayed in the spray cooler, the collection solvent may be cooled to a temperature less than the boiling point of the collection solvent being used. In other examples, the collection solvent cooler, such as 55, may cool the collection solvent to a temperature of approximately 0 to 150 degrees Fahrenheit, 0 to 40 degrees Fahrenheit, 40 to 80 degrees Fahrenheit, 80 to 120 degrees Fahrenheit, to less than 100 Fahrenheit, to less than 120 degrees Fahrenheit, to less than 150 degrees Fahrenheit or other temperature ranges. To the greatest degree possible, all of the internal areas of the system that contact the gas stream as the gas stream passes between the gas stream cooler 50 and the gas stream heater 2 are kept at a temperature that is below the temperature of the gas stream when it exits the gas stream cooler 50, such that collection solvent condenses on these surfaces to wash away any accumulated plant oils. In some examples, the temperature is kept near or below 85 to 145 degrees Fahrenheit. The primary solvent pump 12 pumps collection solvent from the sump area 13 to the collection solvent sprayers 17 in the collection chamber 16 at a rate of approximately 1.0 to 7.0 gallons per minute. Other examples include a rate of 0.0002 to 1.0 gallons per minute, 7.0 to 10.0 gallons per minute, greater than 10.0 gallons per minute, less than 10.0 gallons per minute or other rates. The collection solvent used within the system may be comprised primarily of ethyl alcohol and water at a ratio of approximately 40% ethyl alcohol and 60% water to 95% ethyl alcohol and 5% water. The evacuation pump 24 is operable to maintain a negative system pressure such that the highest pressure area of the gas stream (such as that found at the blower exit) is still kept slightly below that of ambient pressure. In doing such, solvent vapors and/or volatilized plant oils do not readily escape from the seals within the system and must pass through the cold trap 22 where they are condensed and returned to the system. The volume of gas displaced by the evacuation pump 24 is approximately 0.01 to 5.0 cubic feet per minute.

The specific descriptions in this disclosure should not be viewed as limiting the scope of this invention. As a non-limiting example, different heat exchangers may be used, components may be moved around, functions of various components may be combined into one structure or the function of one component may be divided between several components. Further, the arrangements and configurations of elements in FIG. 1 and FIG. 2 are for ease of explanation and are not limiting. As one example, the volatilization chamber 7 is shown with a bottom entrance and a top exit but may have the entrance and exit located elsewhere. Those of skill in the art will recognize that the herein described embodiments of the present invention may be altered in other ways without departing from the scope or teaching of the present invention. As another non-limiting example of one of many ways that the system may be rearranged, in comparison to FIG. 1, the embodiment illustrated in FIG. 2 shows several of the parts of the system rearranged or even eliminated. FIG. 2 shows that the centrifugal droplet separator 20 illustrated in FIG. 1 has been removed. In this embodiment, only a single demisting section 21 is utilized to prevent droplets from entering the heater 2. The steam generator 3 has also been removed in FIG. 2. In this embodiment, electric heating elements are used in the heater section 2. The plant material collection system has also been simplified. Instead of utilizing a secondary entrainment zone 27 and a secondary gas stream 25, the primary plant material separation device drains directly into the processed plant material collection bin 29. An optional airlock valve 58 may be used to keep the processed plant material collection bin 29 separated from the primary gas stream 1. Two gas movers 19 have been used in series to increase the pressure available to propel the gas stream. The placement of one of the gas movers 19 has been moved from the position illustrated in FIG. 1, however, this could be placed directly in front of the second gas mover 19 or elsewhere in the system.

Figure 11:
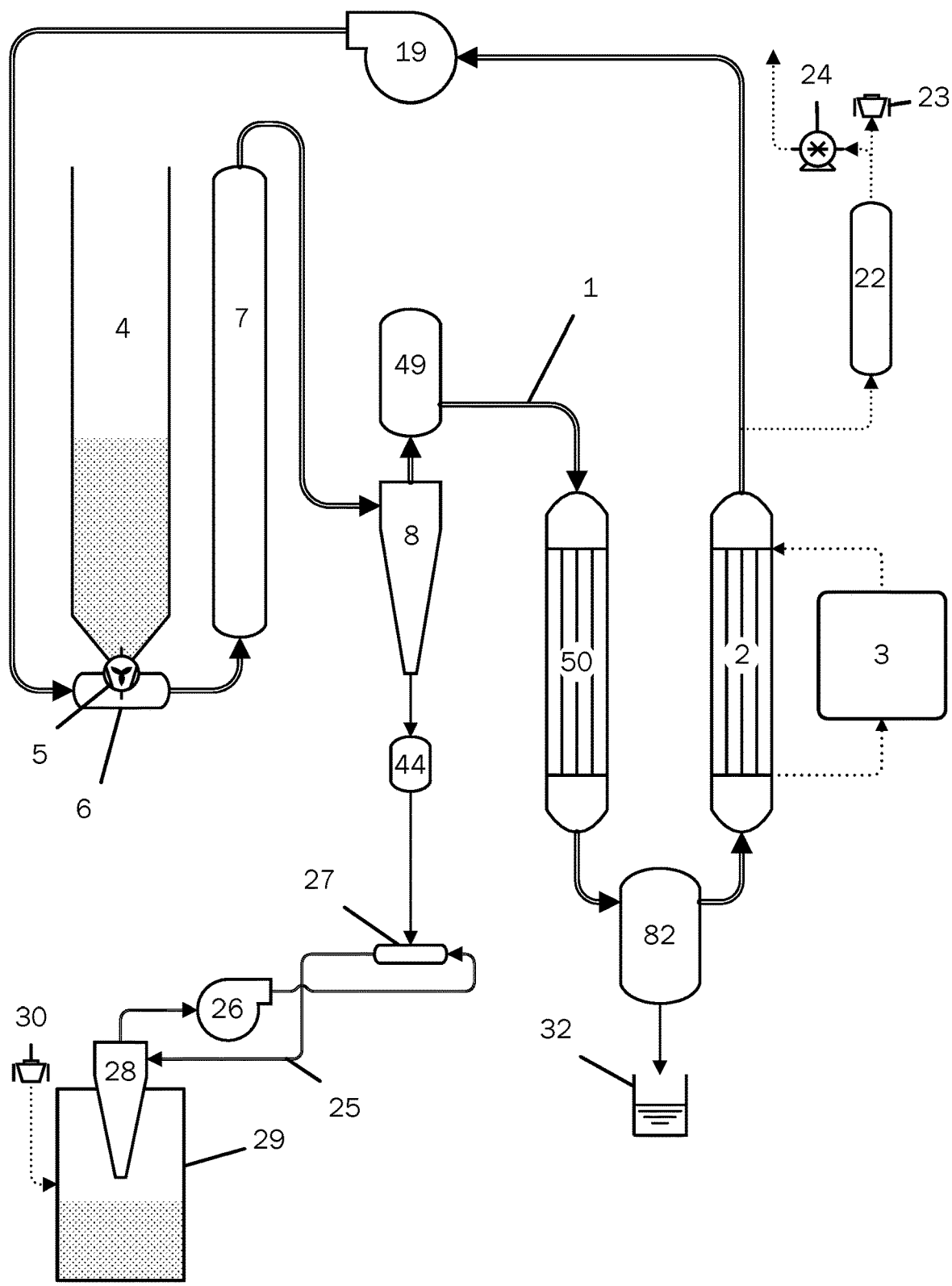
FIG. 11 illustrates a simplified embodiment that uses little or no solvent.

FIG. 11 illustrates an embodiment of the invention that is designed to operate without a collection solvent. This embodiment may be operated with no solvent at all, or with only a minimal amount of a diluting solvent. This embodiment includes a primary gas stream 1, a tube-in-shell steam powered gas stream heater 2, a steam generator 3 to provide steam to the heater, a gas stream mover 19, a hopper 4, a plant material portioning device 5, a primary plant material entrainment zone 6, one or more volatilization chambers 7, a primary plant material separation device 8, a gas stream filter 49, a volatilized oil condenser/gas stream cooler 50, a condensed plant oil gas stream/oil separation device 82, an oil collection area 32, a heated separated plant material exit 44, an air pump 24 capable of removing a portioned amount of gas from the system, a secondary gas stream 25, a secondary gas stream mover 26, a secondary plant material entrainment zone 27, a secondary plant material separation device 28, a processed plant material collection bin 29, and an in-only check valve 30 to allow atmospheric air or a displacing gas into the system via the plant material collection bin 29. Depending on the desired application, any of these components and parts may be duplicated within the system one or more times in series or in parallel or may be eliminated entirely to attain different effects. The order of the components within the system may also be modified to attain different effects. The steam powered heater 2 may also be replaced with an electrically powered heater, a heater with a circulating thermal fluid, or a heater that is powered by other methods. Elements 1, 2, 3, 19, 4, 5, 6, 7, 8, 49, 44, 25, 26, 27, 28, 29, 30, 22, 23, and 24 function in a substantially similar manner to corresponding similar components in previously discussed embodiments of the invention. Element 50, however, functions in a modified way as compared to previously discussed embodiments. Additionally, in some embodiments, the gas stream mover has been placed after the heater such that it remains too hot for plant oils to condense on its inner surfaces. It should be noted that the elements mentioned may also function in a similar way in the embodiments following this section.

The embodiment illustrated in FIG. 11 is designed to use little or no solvent. After the volatilized plant oils travel from the volatilization section 7, through the primary plant material separation device 8 and through the optional gas stream filter 49, they enter a volatilized oil condenser/gas stream cooling section 50. The condenser/gas stream cooler 50 is preferably a tube-in-shell heat exchanger that is cooled by a coolant or coolant mixture, however, any of the condenser designs and cooling methods previously discussed within this document or PCT/IB2014/002383 may be used. As the volatilized oils enter the gas stream condenser/cooler 50, a portion of the volatilized oils condense on the condensation surfaces within the condenser. The volatilized oils that do not condense through the first pass through the condenser may continue to recirculate with the gas stream until they are condensed in successive passes through the condenser 50. The extracted plant oils that condense on the condensation surfaces within the condenser 50 drip down the condenser surfaces and flow out of the condenser 50 into a condensed oil separation section 82 and eventually into the condensed oil collection area 32. The gas stream 1 continues to flow through the system and back through the heater.

It is beneficial to maintain the coolant medium and/or condensation surfaces within the gas stream condenser/gas stream cooler 50 at a temperature that is below the condensation point of the volatilized plant oils being extracted and yet still high enough to keep the plant oils in a runny state so they readily drip and flow out of the bottom of the condenser 50, through the condensed oil separation section 82 and into the condensed oil collection area 32. A few non-limiting temperature examples may include maintaining the condensation surfaces within the condenser between 100 to 300 degrees Fahrenheit, 120 to 280 degrees Fahrenheit, 120 to 150 degrees Fahrenheit, and 320 to 340 degrees Fahrenheit. Other temperatures ranges may also be used.

Figure 12A:
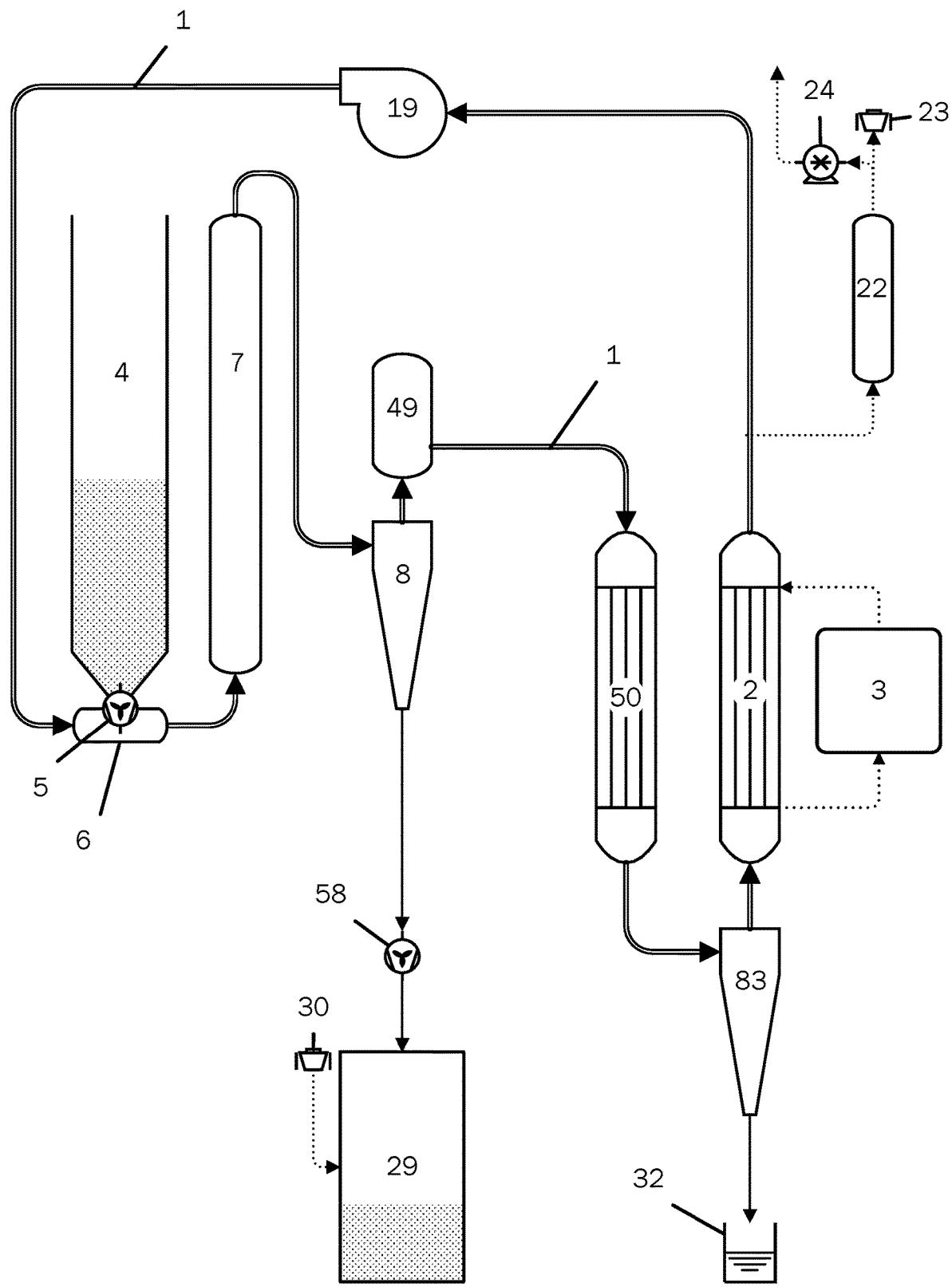
FIG. 12a illustrates an additional embodiment that uses little or no solvent and utilizes a centrifugal oil droplet separator.

FIG. 12a illustrates another embodiment of the invention that needs little or no solvent to function. In this embodiment, a centrifugal condensed oil separator 83 is utilized. The centrifugal oil separator 83 may be a cyclone or other suitable separation device. As the gas stream passes through the gas stream condenser/cooler 50, a portion of the volatilized plant oils will condense on the surfaces within the condenser, however, a portion of the oil may also condense and precipitate into the cooler gas stream as small or microscopic oil droplets that become entrained in the flow of the gas stream. By using a centrifugal oil separator 83, a large portion of these entrained small and microscopic oil droplets are captured within the oil separator prior to being recirculated back through the heater 2. The oil droplets that are captured, along with the oil that drips from the condenser 50, may then drain into the extracted oil collection area 32. In order to illustrate that many of the components within the invention may be rearranged or altered in different applications, the embodiment illustrated in FIG. 12a is shown with a simplified processed plant material collection system as compared to FIG. 11.

Figure 12B:
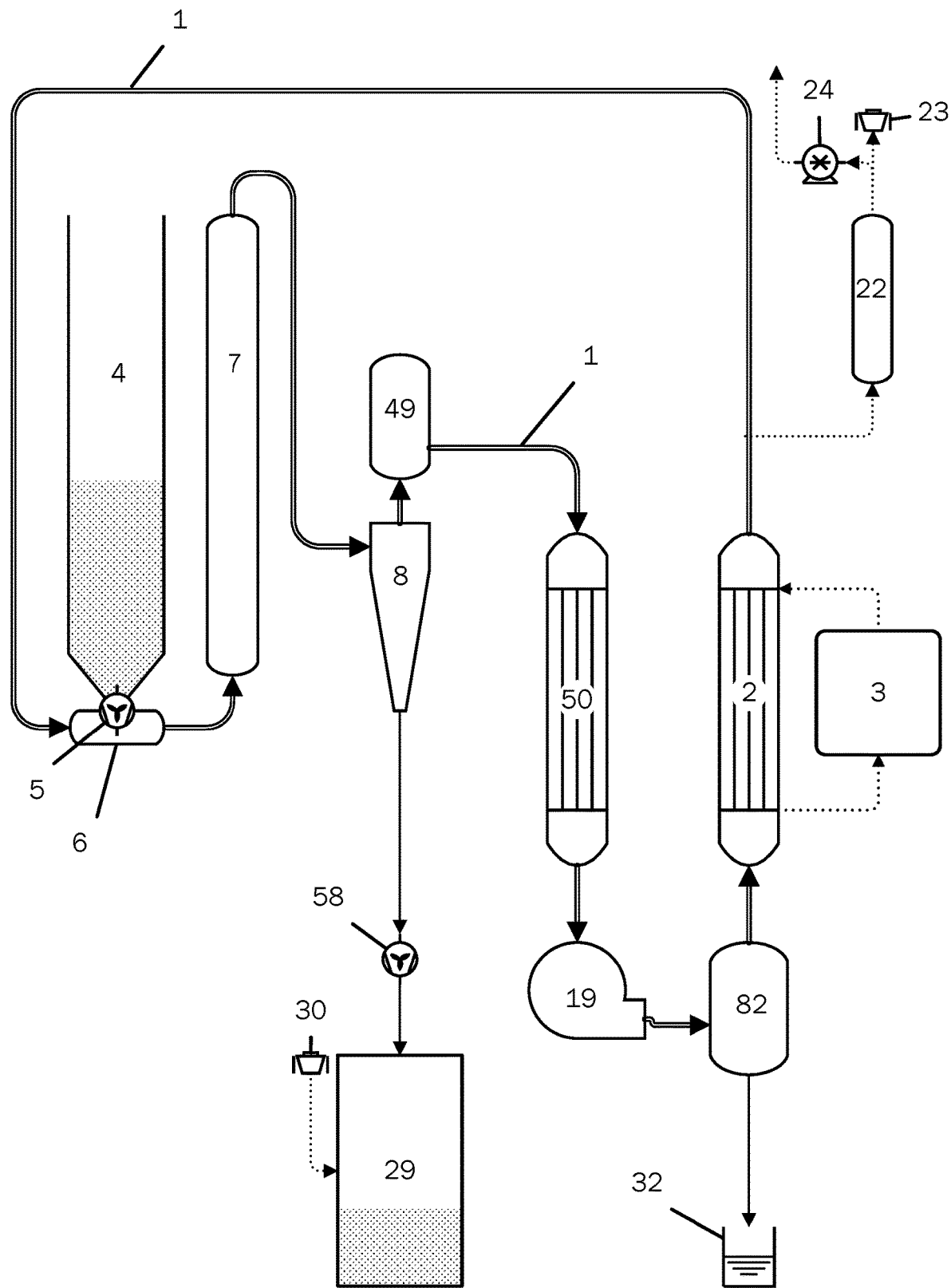
FIG. 12b illustrates an embodiment that uses little or no solvent and utilizes a centrifugal blower as a centrifugal oil droplet separator.

FIG. 12b illustrates an arrangement similar to the embodiment illustrated in FIG. 12a. In this embodiment, the gas stream mover 19 is placed after the condenser/cooler 50 and before the heater 2. An optional condensed oil separation section 82 may be included in this embodiment. It is preferred that the gas stream mover be of a centrifugal blower design, such as, but not limited to a regenerative blower, turbine blower, pressure blower, turbo compressor, centrifugal blower or any other design capable of creating suitable centrifugal forces. By positioning a centrifugal type gas stream mover 19 after the gas stream cooler 50, the gas stream mover 19 serves as a centrifugal oil separator that separates and collects microscopic oil droplets that precipitated into the gas stream after the gas stream was cooled. The oil droplets that are captured in the gas stream mover 19, along with any oil that drips from the condenser 50, may then drain into the extracted oil collection area 32. A gas stream mover with blades (e.g., a turbo compressor, regenerative blower, turbine blower, pressure blower or a gas stream mover with high speed parts) may also collect oil droplets by impingement when the oil droplets collide with surfaces of the blades. Such a blower may be substituted for any of the gas stream mover elements discussed in this document.

In the embodiments illustrated in FIGS. 12*a* and 12*b*, it is preferable that the centrifugal oil separator 83 or centrifugal gas stream mover 19 be maintained at a temperature that is high enough to keep the captured droplets runny and free flowing so the collected oil may flow from the centrifugal capture device, yet cool enough to prevent any of the captured oil droplets from being re-volatilized. It is also preferable that the condenser/gas stream cooler 50 in the embodiments illustrated in FIGS. 12*a* and 12*b* be maintained at a temperature below the condensation point of the volatilized plant oils being extracted and yet still high enough to keep any collected oil in a runny state so they readily drip and flow out of the bottom of the condenser 50 and continue to flow through the system and into the extracted oil collection area 32. In some embodiments illustrated in FIGS. 12*a* and 12*b*, it may be preferred to design the gas stream cooler 50 to minimize the quantity of oil collected in the condenser and rely primarily on the centrifugal separator 83 or centrifugal gas mover 19 as the primary separation device.

Figure 13:
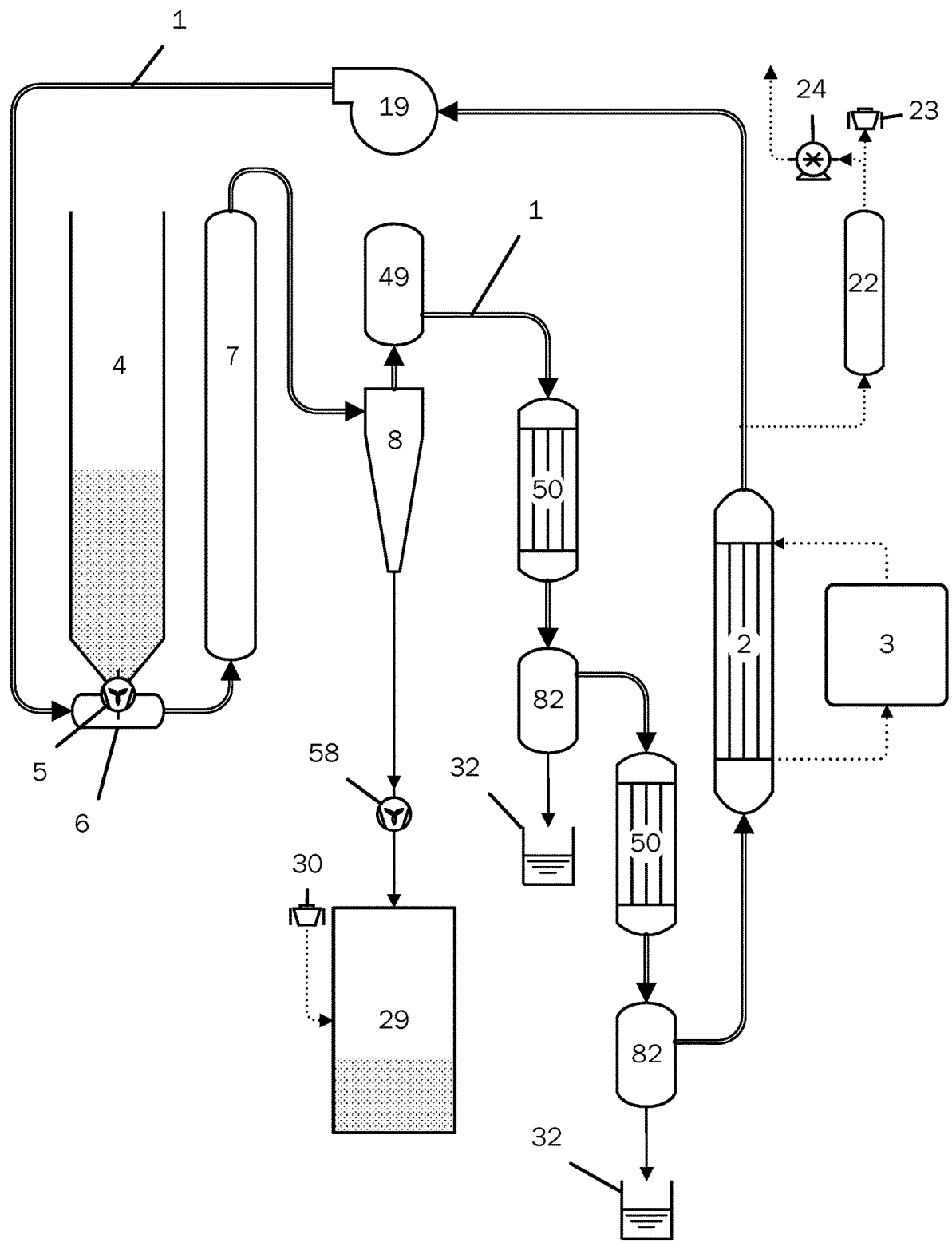
FIG. 13 illustrates an embodiment that uses little or no solvent and also facilitates continuous fractionation of the plant oils being extracted.

FIG. 13 illustrates another embodiment that is designed to use little or no solvent to function. In this embodiment, a set of elements that includes a gas stream condenser/cooler 50, an oil separator 82 and an extracted oil collection area 32 is repeated in series as many times as is practical to remove various fractions from the volatilized oils within the gas stream. With this arrangement, fractionalization of the plant oil constituents may occur in a continuous manner. For ease of explanation, only two sets of gas stream condensers/coolers 50, oil separation sections 82 and extracted oil collection areas 32 are illustrated in FIG. 13, however, this number may be increased. In the embodiment illustrated in FIG. 13, it will be beneficial to set the heater 2 to a temperature that is high enough to volatilize all of the desired fractions within the plant material to be extracted, such that all of the oil fractions become volatilized and travel within the gas stream 1 as volatilized plant oil gasses. The condensation surfaces within the first gas stream condenser/cooler 50 should be maintained at a temperature that is low enough to condense a first fraction of volatilized plant oil constituents and yet is too high to condense other fractions of volatilized plant oil constituents. The first fraction of volatilized plant oils will condense on the condenser surfaces and drain through the first condenser 50, through the first oil separator 82 and into first oil collection area 32. Other fractions within the volatilized oil entrained in the gas stream that have lower condensation points than the first fraction of volatilized plant oils cannot condense within the first condenser 50 and will continue to travel within the gas stream as a volatilized plant oil gas into a second gas stream condenser/cooler 50. The condensation surfaces within the second gas stream condenser/cooler 50 are maintained at a temperature that is lower than the first gas stream condenser/cooler 50 and also low enough to condense a second fraction of volatilized plant oil constituents and yet also too high to condense other volatilized plant oil constituents. This pattern may be repeated with multiple gas stream condenser/coolers as many times as is practical to remove various fractions from the volatilized oils within the gas stream. It is beneficial that the last condenser 50 in the series be maintained at a low enough temperature to condense all of the remaining oil fractions and yet still be kept hot enough to keep the oils flowing freely from the last condenser, through the last oil separator 82 and into the last extracted oil collection area 32.

Figure 14:
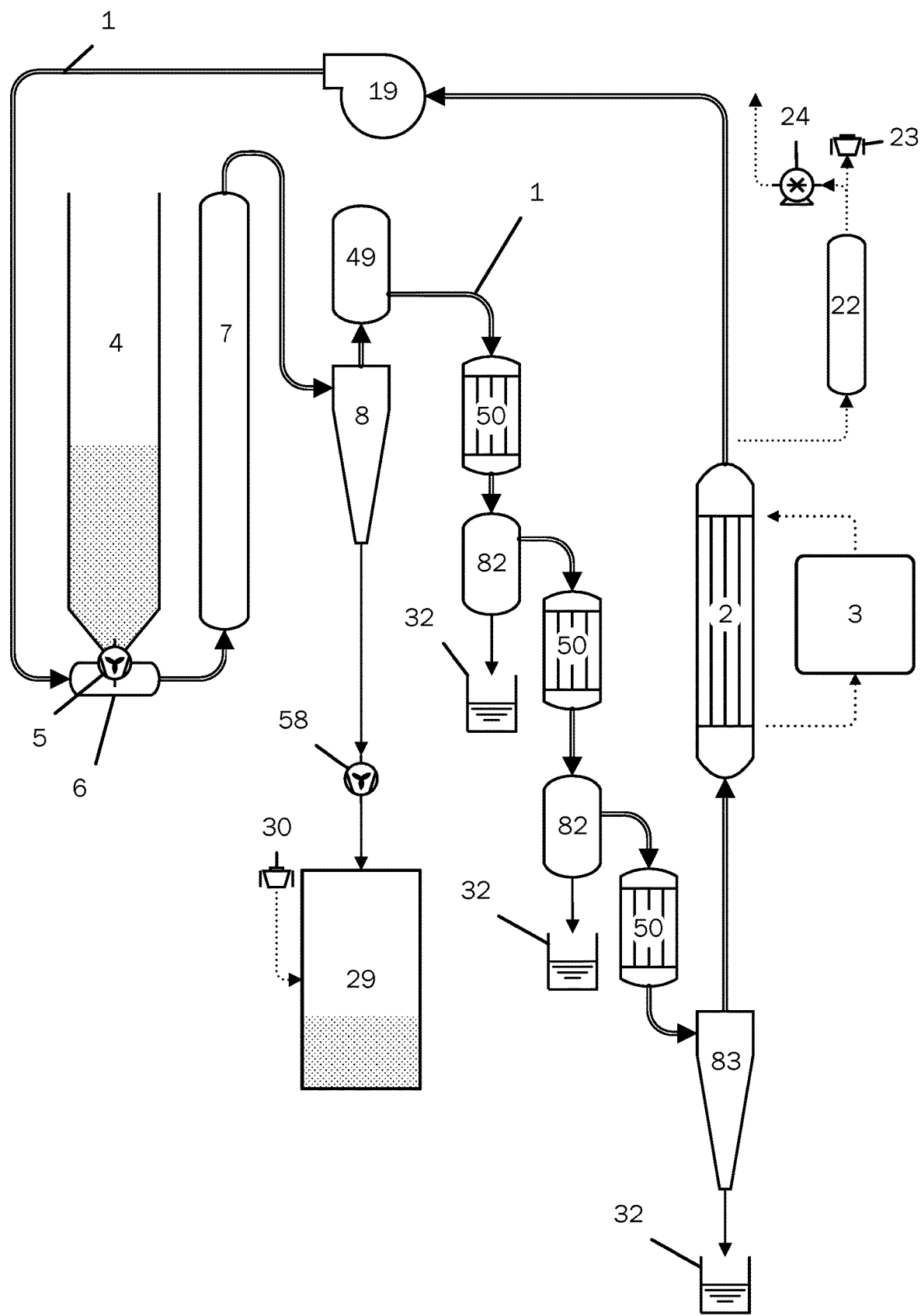
FIG. 14 illustrates an embodiment that uses little or no solvent, facilitates continuous fractionation of the plant oils being extracted and utilizes a centrifugal oil droplet separator.

FIG. 14 illustrates an additional embodiment that enables continuous fractionalization. In this embodiment, the last oil separation device in the series is a centrifugal oil separation device 83, as previously described in the section describing FIG. 12*a*. A centrifugal separation device 83 may be placed after each successive condenser/gas stream cooler 50 to facilitate collection of the fractionated oil components in a similar way as described in FIG. 12*a*.

Figure 15:
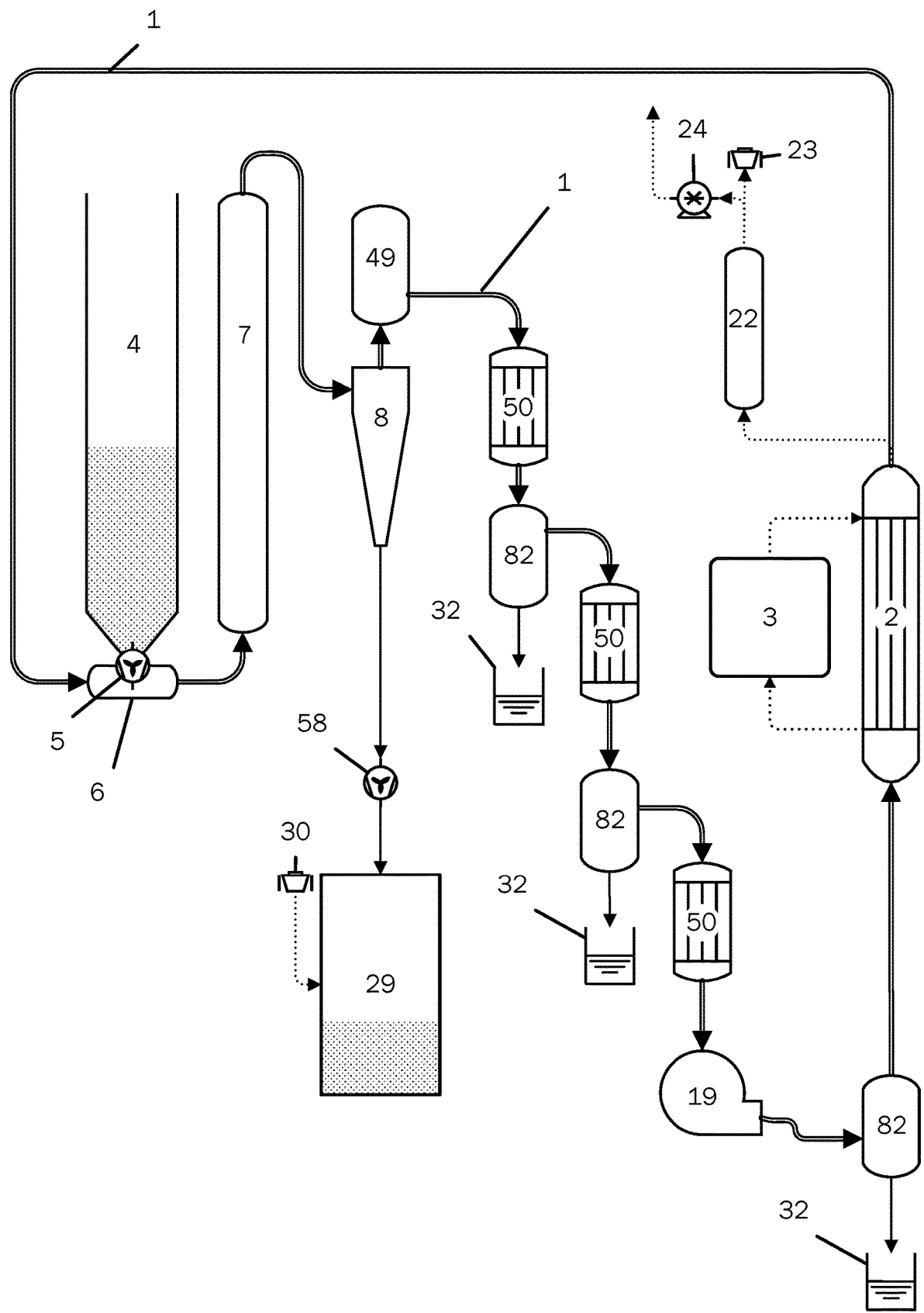
FIG. 15 illustrates an embodiment that uses little or no solvent, facilitates continuous fractionation of the plant oils being extracted and utilizes a centrifugal gas mover as an oil droplet separator.

FIG. 15 illustrates an additional embodiment that enables continuous fractionalization. In this embodiment, the gas stream mover 19 has been relocated to serve as a centrifugal oil separation device. In this embodiment, it is beneficial to utilize a centrifugal type gas stream mover that generates high centrifugal effects. Examples of centrifugal gas movers have been previously discussed in other sections of this disclosure. A few non-limiting examples may include turbo compressors, regenerative blowers, turbo blowers, pressure blowers and other centrifugal devices. A centrifugal gas stream mover 19 may be placed after each successive condenser 50 to facilitate collection of the fractionated oil components.

As non-limiting examples of potential temperatures that may be utilized in the embodiments illustrated in FIGS. 13, 14, and 15, the following approximate temperatures may be beneficial: The internal areas of the volatilization chamber may be heated to a temperature between 356 and 440 degrees Fahrenheit to volatilize all of the desired fractions of plant oil to be extracted. The condensation surfaces within a first gas stream condenser/cooler 50 may be maintained between 366 and 427 degrees Fahrenheit. The condensation surfaces within a second gas stream condenser/cooler may be maintained between 357 and 364 degrees Fahrenheit. The condensation surfaces within a third gas stream condenser/cooler 50 may be maintained between 316 and 355 degrees Fahrenheit. The condensation surfaces within a fourth gas stream condenser/cooler 50 may be maintained between 290 and 314 degrees Fahrenheit. The condensation surfaces within a final gas stream condenser/cooler 50 may be maintained between 110 and 289 degrees Fahrenheit. Other temperatures and numbers of repeating components may be used in other embodiments and examples.

As alternative non-limiting examples of potential temperatures that may be utilized in the embodiment illustrated in FIGS. 13, 14 and 15 the following approximate temperatures may be beneficial: The internal areas of the volatilization chamber may be heated to a temperature between 356 and 400 degrees Fahrenheit to volatilize all of the desired fractions of plant oil to be extracted. The condensation surfaces within a first gas stream condenser/cooler 50 may be maintained between 357 and 364 degrees Fahrenheit. The condensation surfaces within a second gas stream condenser/cooler may be maintained between 316 and 355 degrees Fahrenheit. The condensation surfaces within a third gas stream condenser/cooler 50 may be maintained between 290 and 314 degrees Fahrenheit. The condensation surfaces within a final gas stream condenser/cooler 50 may be maintained between 110 and 289 degrees Fahrenheit. Other temperatures and numbers of repeating components may be used in other embodiments and examples.

Figure 16:
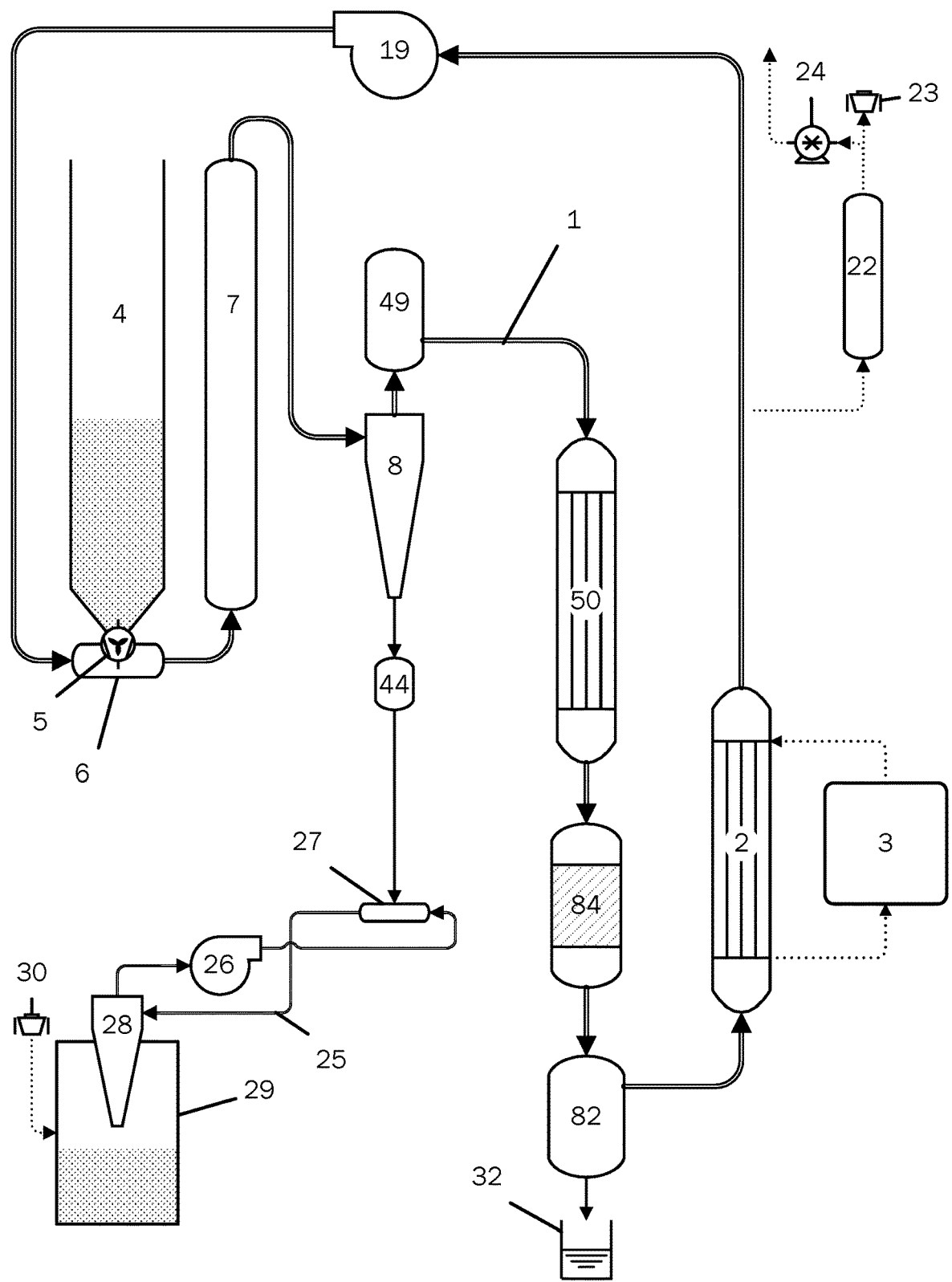
FIG. 16 illustrates an embodiment that uses little or no solvent and utilizes electrostatic collection plates to facilitate removal of plant oils from the gas stream.

FIG. 16 illustrates an embodiment that utilizes an electrostatic collector 84 to efficiently remove plant oil from the gas stream. As the gas stream passes through the gas stream condenser/cooler 50, a portion of the volatilized plant oils may condense on the surfaces within the condenser and drip down through the system and into the extracted oil collection area 32, while another portion of the oil may condense and precipitate into the cooler gas stream as small or microscopic oil droplets that become entrained in the flow of the gas stream. By using an electrostatic collector 84, a large portion of these entrained small and microscopic oil droplets may be captured within the electrostatic collector prior to being recirculated back through the heater 2. As the gas stream and entrained small and microscopic plant oil droplets pass from the gas stream condenser 50 and enter the electrostatic collector 84, the electrostatic collector 84 imparts an electrostatic charge to the entrained oil droplets. The collection surfaces within the electrostatic collector 84 are charged with an opposite electrostatic charge from the oil droplets. As the entrained oil droplets pass near the collection surfaces, the oil droplets are electrically attracted to the collection surfaces. As the oil droplets collect on the collection surfaces, they begin to coalesce into larger droplets that drip from the electrostatic collection surfaces and drain through the system into the extracted oil collection area 32. The design and function of electrostatic collectors will be known to those of skill in the art.

In the embodiment illustrated in FIG. 16, it is beneficial that the condensation surfaces within the gas stream condenser/cooler 50 be maintained at a temperature below the condensation point of the volatilized plant oils being extracted and yet high enough to keep the plant oils in a runny state so they readily drip and flow out of the bottom of the condenser 50, through the electrostatic collector 84, through the condensed oil separation section 82 and into the condensed oil collection area 32. In order for collected plant oils to easily flow from the electrostatic collector 84, it is beneficial that the gas stream exiting the gas stream condenser/cooler 50 be maintained at a temperature that keeps the surfaces of the electrostatic collector 84 warm enough that collected oil may freely drip from the electrostatic collection surfaces and drain down through the system to the oil collection area 32. A few non-limiting temperature examples may include maintaining the condensation surfaces within the condenser 50 and electrostatic collector area 84 between 100 to 300 degrees Fahrenheit, 120 to 280 degrees Fahrenheit, 120 to 150 degrees Fahrenheit, and 320 to 340 degrees Fahrenheit. In some embodiments illustrated in FIG. 16, it may be preferred to design the condenser/gas stream cooler 50 to minimize the quantity of oil collected in the gas stream cooler 50 and rely primarily on the electrostatic collector 84 as the primary oil collection/separation device.

Figure 17:
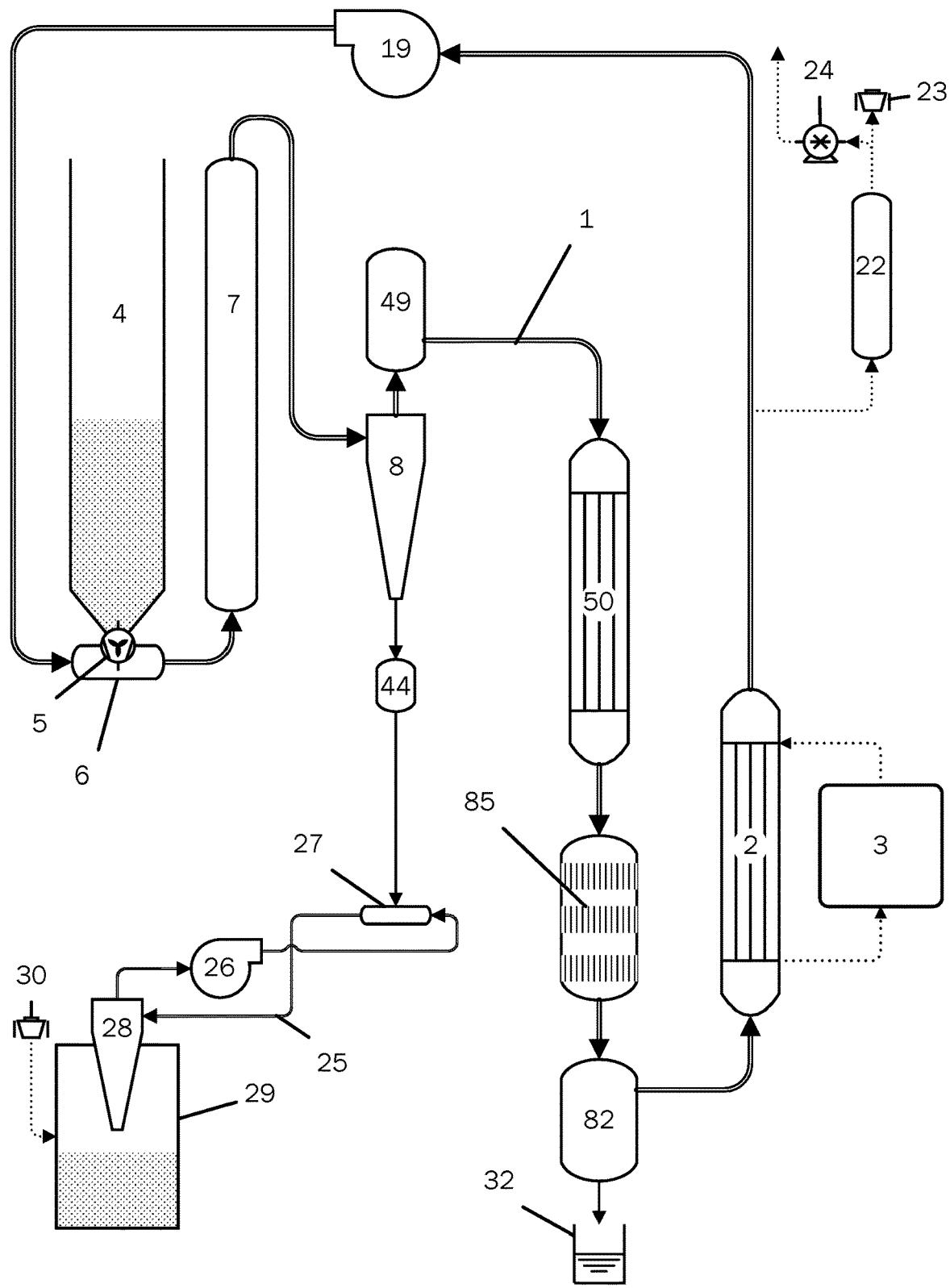
FIG. 17 illustrates an embodiment that uses little or no solvent and utilizes demisting pads and/or packing material to facilitate removal of plant oils from the gas stream.

FIG. 17 illustrates an embodiment that utilizes a filtration section 85 that includes filters, demisting pads and/or packing material to remove small and microscopic oil droplets from the gas stream. The mediums contained in the filtration section 85 are designed to function with little or no solvent. Since there may be little or no solvent present, it is preferred that the filtration section be maintained at a temperature that keeps the collected oil runny and free flowing so as to allow the oil to easily drip from the filter and/or demisting pads and into the extracted oil collection area 32. As the gas stream passes through the gas stream condenser/cooler 50, a portion of the volatilized plant oil may condense on surfaces within the condenser and drip down through the system and into the extracted oil collection area 32, while another portion of the oil may condense and precipitate into the cooler gas stream as small or microscopic oil droplets that become entrained in the flow of the gas stream. As the gas stream and entrained small and microscopic plant oil droplets pass from the gas stream condenser 50 and pass through the filtration section 85, a portion of the entrained oil droplets may be removed from the gas stream. The filtration material may comprise a number of materials, such as, but not limited to sintered glass filters, sintered ceramic filters, sintered metal filters, ceramic filters, other filter designs, random and/or inert packing including raschig rings, saddles and beads made of glass, ceramics, metals, other random and/or inert packing materials such as sand, alumina, gravel, PTFE fibers, stainless steel wool, glass fibers or mineral wool fibers, and structured packing such as knitted packing, woven wire mesh, stainless steel wool, stainless steel matting, woven stainless steel mesh, corrugated metal sections, bubble-cap plates and sieve tray plates or other types of packing to capture the volatilized plant oils. The demisting material may comprise any of the preceding materials, or the demisting material may comprise a structured demister design, corrugated plates demister design, or other design.

Portions of the systems in FIGS. 11, 12a, 12b, 13, 14, 15, 16 and 17 may be heated and/or insulated to assist in achieving target temperatures and/or to prevent condensation in certain areas of the system.

Any of the embodiments illustrated in FIGS. 11, 12a, 12b, 13, 14, 15, 16 and 17 and discussed in their accompanying text may use little or no solvent to function. In some cases, it may be preferred to use no-solvent. In some cases, it may be preferred to use a minimal amount of solvent, not as a primary collection method, but as a diluent or thinning agent to maintain a liquefied oil in a free-flowing state such that it freely drains from the invention's various collection and separation devices. In cases where a minimal amount of solvent is utilized, the general goal is to use as little as possible. A few non-limiting examples would be to use a sufficient amount of solvent such that the collected oils can be measured to contain 25% or less solvent by weight, 15% or less solvent by weight or 10% or less solvent by weight. It may also be advantageous in some cases to maintain a certain level of dissolved solvent in the gas stream. A few non-limiting examples would be to use a sufficient amount of solvent such that the gas stream can be measured to contain 25% or less solvent vapor by weight, 15% or less solvent vapor by weight or 10% or less solvent vapor by weight. In other cases, it may be preferred to maintain a much higher ratio of diluting solvent to ensure that the collected oils do not become too thick to be removed from the system.

The introduction of diluting solvent to the embodiments illustrated in FIGS. 11, 12a, 12b, 13, 14, 15, 16 and 17 may be before and/or within the gas stream cooler 50, before and/or within the centrifugal collection device section 83, before and/or within the centrifugal gas stream mover collection section 19, before and/or within the electrostatic collection section 84, before and/or within the filter collection section 85, before and/or within the oil separation section 82, and/or within other sections of the system. In some embodiments, it may be advantageous to introduce the diluting solvent as a vapor instead of a liquid, with the point of introduction being placed in any of the sections previously stated, within the gas stream 1, within the gas stream heater 2, within the extraction chamber 7, within the gas stream mover 19, within the gas stream filter 49, within the plant material separation device 8, and/or anywhere within the system. The method of introduction of a diluting solvent may be via a nozzle, tube, sprayer, valve, gas injector or any other method known to those of skill in the art or described in other parts of this disclosure.

The diluting solvent utilized in the embodiments illustrated in FIGS. 11, 12a, 12b, 13, 14, 15, 16 and 17 may consist of ethanol, a mixture of ethanol and water, or may consist of any of compounds that are used as collection solvents in any other embodiments described within this disclosure or PCT/IB2014/002383, or other solvents, or a mixture of various solvents. It is preferred that the diluting solvent be food or medical grade, however any suitable diluting solvent may be used. If ethanol is introduced as the diluting solvent, a few non-limiting examples may to introduce an ethanol diluting solvent that is about 100% ethanol, about 95% ethanol and 5% water, about 90% ethanol and 10% water, about 85% ethanol and 15% water, about 80% ethanol and 20%, water, about 75% ethanol and 25% water, about 70% ethanol and 30% water, about 65% ethanol and 35% water, about 60% ethanol and 40% water, about 55% ethanol and 45% water, about 50% ethanol and 50% water, or ethanol and water at other ratios. Alternatively, if ethanol is introduced as the diluting solvent, a mixture of ethanol and water may be introduced with an ethanol concentration that is greater than 40% ethanol, greater than 50% ethanol, greater than 55% ethanol, greater than 65% ethanol, greater than 70% ethanol, greater than 75% ethanol, greater than 80% ethanol, greater than 85% ethanol, greater than 90% ethanol or greater than 95% ethanol. Ethanol may also be mixed with other solvents at various ratios. The specific descriptions in this disclosure should not be viewed as limiting the scope of this invention. The elements within the embodiments illustrated in FIGS. 11, 12a, 12b, 13, 14, 15, 16 and 17, along with other elements discussed in the text describing the same, or elements discussed in text or illustrated in figures from any other section of this disclosure, may be rearranged in different orders within the system, combined with different elements described in other embodiments, repeated in parallel or in series, or may be eliminated entirely in some embodiments. As a non-limiting example, different heat exchangers and heaters may be used, components may be moved around, functions of various components may be combined into one structure or the function of one component may be divided between several components. Further, the arrangements and configurations of elements in FIGS. 11, 12a, 12b, 13, 14, 15, 16 and 17 are for ease of explanation and are not limiting. As one example, the volatilization chamber 7 is shown with a bottom entrance and a top exit but may have the entrance and exit located elsewhere. It should be noted that the gas stream condenser/cooler 50 and electrostatic collector 84 may be combined into the same section in some embodiments. It should also be noted that the gas stream heater 2 may be powered by electric heating elements instead of steam or a heated fluid. Other condenser designs may be used. Any of the components described in FIGS. 11, 12a, 12b, 13, 14, 15, 16 and 17 and their accompanying text may be modified in any way that similar components are described in other embodiments within this disclosure, PCT/IB2014/002383, or in other ways that are generally known to those of skill in the art. Additionally, in some cases, it may be advantageous to operate the embodiments in FIGS. 11, 12a, 12b, 13, 14, 15, 16 and 17 as open systems. In cases where the embodiments illustrated in FIGS. 11, 12a, 12b, 13, 14, 15, 16 and 17 are operated as open systems, it is preferable that the system be open after the final oil droplet separator/collection device (83, 19, 84, 85 or 82) and before the heater 2.

In some aspects, the disclosure relates to a method of extracting oil from plant material. The method may comprise providing a system for extracting oil from plant material. The system may comprise a gas moving device operable to propel a gas stream through the system. The system may comprise an extraction chamber in communication with the gas moving device such that the gas stream is directed through the extraction chamber. The system may comprise a condensation surface in communication with the gas moving device such that the gas stream is directed to the condensation surface.

The gas moving device may or may not be a centrifugal separator. The gas mover may or may not comprise a compressed air tank or a liquefied gas, such as liquid nitrogen.

The condensation surface may be a surface configured to allow the portion of oil to flow along the surface to allow collection of the oil. The condensation surface may therefore comprise chemical and/or mechanical properties that allow the portion of oil to flow. A condensation surface that allows the portion of oil to flow provides an advantage over existing systems because it allows methods that use less solvent.

The system may comprise a centrifugal separator, which may comprise the condensation surface. The centrifugal separator may or may not be the gas moving device of the system. The centrifugal separator may comprise at least one blade and an axis of rotation, e.g., such that the at least one blade rotates about the axis, or the centrifugal separator may comprise a device with no blades at all. The method may further comprise rotating the blade about the axis. The condensation surface may comprise the at least one blade and/or may comprise a surface of the centrifugal separator other than a blade such as the housing of the separator. Contacting the gas stream with the condensation surface may cause the portion of oil to collect on a blade, housing, and/or other surface of the centrifugal separator. The method may further comprise maintaining the at least one blade at both a temperature and an angular velocity that results in a centrifugal force that is greater than the resistance of the portion of the oil to flow. The rotation of the blade about the axis may thereby provide a mechanical force that causes the portion of the oil to flow such that the oil may be collected.

In some embodiments, the condensation surface does not comprise a blade of the centrifugal separator. For example, a system may comprise a centrifugal separator that lacks blades, or a system may comprise a centrifugal separator having one or more blades wherein the condensation surface does not comprise the one or more blades.

The system may comprise a condensation surface that is heated and/or angled to allow the portion of oil to flow. A method may comprise maintaining a condensation surface at an angle and temperature that result in a parallel component of gravitational force that is greater than the resistance of the portion of the oil to flow. The condensation surface may be angled of about $-90°$ to about $90°$ relative to the force of gravity, such as about $-90°$ to about $-70°$, about $-80°$ to about $-600$, about $-70°$ to about $-50°$, about $-60°$ to about $-40°$, about $-50°$ to about $-30°$, about $-40°$ to about $-20°$, about $-30°$ to about $-10°$, about $-20°$ to about $0°$, about $-10°$ to about $10°$, about $0°$ to about $20°$, about $10°$ to about $30°$, about $20°$ to about $40°$, about $30°$ to about $50°$, about $40°$ to about $60°$, about $50°$ to about $70°$, about $60°$ to about $80°$, or about $70°$ to about $90°$. Surfaces of less than $0°$ to about $-90°$ are ceilings, a surface of $0°$ is a wall that is parallel to the force of gravity, and surfaces of greater than $0°$ to less than $90°$ are inclined planes. The condensation surface may be angled at about $-90°$ to about $60°$, about $0°$ to about $60°$, about $0°$ to about $45°$, or about $-45°$ to about $45°$ relative to the force of gravity.

A condensation surface may comprise an electrostatic charge. The electrostatic charge may be sufficient to capture and remove a portion of the oil from the gas stream. The method may further comprise condensing the portion of the oil into oil droplets that become entrained in the gas stream after volatizing the oil. In some embodiments, the method comprises charging the oil droplets with an electrostatic charge (e.g., a charge that is opposite from the charge of the condensation surface). Contacting the gas stream with the condensation surface may comprise contacting the charged oil droplets with the condensation surface.

A condensation surface may comprise a filter medium and/or demisting pad. The filter medium and/or demisting pad may be sufficient to capture and remove a portion of the oil from the gas stream. The method may further comprise condensing the portion of the oil into oil droplets that become entrained in the gas stream after volatizing the oil.

In some embodiments, the temperature of a condensation surface, centrifugal separator, centrifugal capture device, centrifugal gas stream mover, electrostatic collector, filter section, condenser, and/or gas stream cooler is about 100° F. to about 300° F., about 110° F. to about 289° F., about 120° F. to about 280° F., about 120° F. to about 150° F., about 290° F. to about 314° F., about 316° F. to about 355° F., about 320° F. to about 340° F., about 357° F. to about 364° F., or about 366° F. to about 427° F. The temperature of a condensation surface, centrifugal separator, centrifugal capture device, centrifugal gas stream mover, electrostatic collector, filter section, condenser, and/or gas stream cooler may be about 100° F. to about 315° F., about 100° F. to about 212° F., or about 120° F. to about 315° F. The temperature of a condensation surface, centrifugal separator, centrifugal capture device, centrifugal gas stream mover, electrostatic collector, filter section, condenser, and/or gas stream cooler may be about 100° F. to about 140° F., about 120° F. to about 160° F., about 140° F. to about 180° F., about 160° F. to about 200° F., about 180° F. to about 220° F., about 200° F. to about 240° F., about 220° F. to about 260° F., about 240° F. to about 280° F., about 260° F. to about 300° F., about 280° F. to about 320° F., about 300° F. to about 340° F., about 320° F. to about 360° F., about 340° F. to about 380° F., about 360° F. to about 400° F., about 380° F. to about 420° F., or about 400° F. to about 440° F.

A system may comprise more than one condensation or collection surface, and one condensation or collection surface may be kept at a different temperature than another condensation or collection surface. In such embodiments, any of the temperature ranges infra may be used interchangeably with different components. As a non-limiting example, it may be preferred to keep the temperature of the condenser/gas stream cooler section 50 within a higher temperature range than the centrifugal collection device section 83, centrifugal gas stream mover collection section 19, electrostatic collection section 84 or filter collection section 85, and, in some cases, it may be preferred to keep the temperature of the condenser/gas stream cooler section 50 within a lower temperature range than the centrifugal collection device section 83, centrifugal gas stream mover collection section 19, electrostatic collection section 84 or filter collection section 85.

In general, it is desirable to maintain the collection surfaces of the embodiments illustrated in FIGS. 11, 12a, 12b, 13, 14, 15, 16 and FIG. 17 hot enough such that collected oils are able to flow from each of the collection surfaces. In some cases, it may be desirable to keep the gas stream cooler/condenser colder to facilitate efficient precipitation of the volatilized oils into small and or microscopic droplets to facilitate removal with the centrifugal separation device or centrifugal gas stream mover. In such cases, it may be desirable to keep the surfaces of the gas stream cooler at about −100 to about −50° F., about −50 to about −25° F., about −25 to about 0° F., about 0 to about 25° F., about 25 to about 50° F., about 50 to about 75° F., or about 75 to about 100° F., or at other temperatures when desirable. The centrifugal collection device section 83, centrifugal gas stream mover collection section 19, electrostatic collection section 84 or filter collection section 85 may be kept at a warmer temperature during operation through active heating (for example, at one of the warmer temperature ranges described), or may be allowed to assume the temperature of the gas stream after it has passed through the cooler and then be intermittently heated during or after operation to facilitate removal of the collected oils. Additionally, if the gas stream cooler is found to collect oils that are too cold to flow, it also may be intermittently heated during or after operation to allow the collected oils to flow from the gas stream cooler/condenser section 50.

The method may comprise maintaining the temperature of the condensation surface at about 100° F. to about 300° F., about 110° F. to about 289° F., about 120° F. to about 280° F., about 120° F. to about 150° F., about 290° F. to about 314° F., about 316° F. to about 355° F., about 320° F. to about 340° F., about 357° F. to about 364° F., or about 366° F. to about 427° F. In some embodiments, the method comprises maintaining the temperature of the condensation surface at about 100° F. to about 315° F., about 100° F. to about 212° F., or about 120° F. to about 315° F. The method may comprise maintaining the temperature of the condensation surface at about 100° F. to about 140° F., about 120° F. to about 160° F., about 140° F. to about 180° F., about 160° F. to about 200° F., about 180° F. to about 220° F., about 200° F. to about 240° F., about 220° F. to about 260° F., about 240° F. to about 280° F., about 260° F. to about 300° F., about 280° F. to about 320° F., about 300° F. to about 340° F., about 320° F. to about 360° F., about 340° F. to about 380° F., about 360° F. to about 400° F., about 380° F. to about 420° F., or about 400° F. to about 440° F.

In some cases, the preferred method may be to keep some condensation or collection surfaces at different temperatures than other condensation or collection surfaces. In such cases, any of the temperature ranges infra may be used interchangeably with different components. As a non-limiting example, it may be preferred to keep the temperature of the condenser/gas stream cooler 50 within a higher temperature range than the centrifugal collection device section 83, centrifugal gas stream mover collection section 19, electrostatic collection section 84 or filter collection section 85, and, in some cases, it may be preferred to keep the temperature of the condenser/gas stream cooler 50 within a lower temperature range than the centrifugal collection device section 83, centrifugal gas stream mover collection section 19, electrostatic collection section 84 or filter collection section 85.

In some embodiments, cooling the gas stream containing the oil comprises cooling the gas stream to a temperature that is at least about 5° F., 10° F., 15° F., 20° F., 25° F., 30° F., 35° F., 40° F., 45° F., or 50° F. lower than the temperature of the condensation surface. The relatively lower temperature of the gas stream may help condense the gas whereas the relatively higher temperature of the condensation surface may help ensure that the oil remains fluid enough to be collected. Similarly, in some embodiments, cooling the gas stream containing the oil comprises cooling the gas stream to a temperature that is at least about 5° F., 10° F., 15° F., 20°

F., 25° F., 30° F., 35° F., 40° F., 45° F., or 50° F. higher than the temperature of the condensation surface. The relatively higher temperature of the gas stream may help ensure that the oil does not condense prior to contacting the condensation surface. Still, in some embodiments, it may be preferable to cool the gas stream containing the oil to a temperature that is about the same temperature as the temperature of the condensation surface.

A method may comprise changing the temperature of the condensation surface. For example, a method may comprise increasing the temperature of the condensation surface. The temperature may be increased to decrease the resistance of the portion of the oil to flow, e.g., to increase the rate at which the oil is collected from the condensation surface. The temperature may be increased, for example, in response to oil build-up on the condensation surface. Similarly, a method may comprise decreasing the temperature of the condensation surface. The temperature may be decreased, for example to increase the rate at which the condensation surface captures and removes the portion of oil from the gas stream.

The method may comprise providing a plant material in the extraction chamber, propelling the gas stream through the extraction chamber, and volatizing an oil from the plant material such that the oil is extracted from the plant material and into the gas stream. In some embodiments, the method may comprise cooling the gas stream containing the oil and propelling the gas stream containing the oil to the condensation surface. The method may comprise contacting the gas stream with the condensation surface thereby capturing and removing a portion of the oil from the gas stream. In some embodiments, the method may comprise collecting the portion of the oil from the condensation surface thereby producing a collected oil.

In some aspects, the gas stream may comprise less than about 30%, about 25%, about 20%, about 15%, about 10%, about 9%, about 8%, about 7%, about 6%, about 5%, about 4%, about 3%, about 2%, or about 1% solvent vapor by weight. The gas stream may comprise less than about 30%, about 25%, about 20%, about 15%, about 10%, about 9%, about 8%, about 7%, about 6%, about 5%, about 4%, about 3%, about 2%, or about 1% solvent vapor by weight prior to propelling the gas stream through the extraction chamber, after propelling the gas stream through the extraction chamber, prior to volatizing the oil, after volatizing the oil, prior to cooling the gas stream, after cooling the gas stream, prior to contacting the gas stream with the condensation surface, after contacting the gas stream with the condensation surface, prior to collecting the portion of oil, and/or after collecting the portion of oil.

In some aspects, the portion of the oil captured and removed from the gas stream may comprise less than about 30%, about 25%, about 20%, about 15%, about 10%, about 9%, about 8%, about 7%, about 6%, about 5%, about 4%, about 3%, about 2%, or about 1% solvent by weight. The portion of the oil captured and removed from the gas stream may comprise less than about 30%, about 25%, about 20%, about 15%, about 10%, about 9%, about 8%, about 7%, about 6%, about 5%, about 4%, about 3%, about 2%, or about 1% solvent by weight after contacting the gas stream with the condensation surface, prior to collecting the portion of oil, and/or after collecting the portion of oil. In some aspects, the collected oil may comprise less than about 30%, about 25%, about 20%, about 15%, about 10%, about 9%, about 8%, about 7%, about 6%, about 5%, about 4%, about 3%, about 2%, or about 1% solvent by weight.

It should be noted that in some embodiments, it may be advantageous to introduce higher ratios of dilution solvent to dilute the collected oils and prevent the collected oils from becoming too thick to leave the system. In such embodiments, the ratio of solvent to oil may be increased to any higher ratio as needed.

In some aspects, the portion of the oil captured and removed from the gas stream may comprise a dilution solvent to oil ratio of about 25:1 to 20:1, about 20:1 to 15:1, about 15:1 to about 10:1, about 10:1, about 9:1, about 8:1, about 7:1, about 6:1, about 5:1, about 4:1 about 3:1 about 2:1 or about 1:1. The portion of the oil captured and removed from the gas stream may comprise a solvent to oil ratio of about 25:1 to 20:1, about 20:1 to 15:1, about 15:1 to about 10:1, about 10:1, about 9:1, about 8:1, about 7:1, about 6:1, about 5:1, about 4:1 about 3:1 about 2:1 or about 1:1 after contacting the gas stream with the condensation surface, prior to collecting the portion of oil, and/or after collecting the portion of oil. In some aspects, the collected oil may comprise a solvent to oil ratio of about 25:1 to 20:1, about 20:1 to 15:1, about 15:1 to about 10:1, about 10:1, about 9:1, about 8:1, about 7:1, about 6:1, about 5:1, about 4:1 about 3:1 about 2:1 or about 1:1.

In some aspects, the gas stream may comprise a dilution solvent to oil ratio of about 25:1 to 20:1, about 20:1 to 15:1, about 15:1 to about 10:1, about 10:1, about 9:1, about 8:1, about 7:1, about 6:1, about 5:1, about 4:1 about 3:1 about 2:1 or about 1:1. The gas stream may comprise a solvent to oil ratio of about 25:1 to 20:1, about 20:1 to 15:1, about 15:1 to about 10:1, about 10:1, about 9:1, about 8:1, about 7:1, about 6:1, about 5:1, about 4:1 about 3:1 about 2:1 or about 1:1 prior to propelling the gas stream through the extraction chamber, after propelling the gas stream through the extraction chamber, prior to volatizing the oil, after volatizing the oil, prior to cooling the gas stream, after cooling the gas stream, prior to contacting the gas stream with the condensation surface, after contacting the gas stream with the condensation surface, prior to collecting the portion of oil, and/or after collecting the portion of oil. The gas stream, portion of the oil, and/or collected oil may comprise little solvent, and/or the gas stream, portion of the oil, or collected oil may be essentially free of solvent. "Essentially free" means that the gas stream, portion of the oil, and/or collected oil may contain unavoidable impurities from the starting materials (e.g., plant material and gas stream) but that the gas stream, portion of the oil, or collected oil are otherwise free from solvent. In some embodiments, the gas stream, portion of the oil, and/or collected oil comprise no solvent. The gas stream, portion of the oil, and/or collected oil may be essentially free of isobutane, ethanol, and/or chloroform.

In some embodiments, contacting the gas stream with the condensation surface comprises contacting a vapor of the oil with the condensation surface. Contacting the gas stream with the condensation surface may cause the portion of the oil to condense on the condensation surface.

In some embodiments, the method further comprises condensing the portion of the oil into oil droplets that become entrained in the gas stream after cooling the gas stream. Contacting the gas stream with the condensation surface may comprise contacting the oil droplets with the condensation surface, which may cause the oil droplets to collect on the condensation surface.

Cooling the gas stream may comprise cooling the gas stream to about 100 to about 300° F., about 110 to about 289° F., about 120 to about 280° F., about 120 to about 150-F, about 290 to about 314° F., about 316 to about 355° F., about 320 to about 340° F., about 357 to about 364° F., or about 366 to about 427° F. In some embodiments, cooling the gas stream comprises cooling the gas stream to about 98.6 to about 314.6° F., about 98.6 to about 212.0° F., or about 122.0 to about 314.6° F. Cooling the gas stream may comprise cooling the gas stream to about 100° F. to about 140° F., about 120° F. to about 160° F., about 140° F. to about 180° F., about 160° F. to about 200° F., about 180° F. to about 220° F., about 200° F. to about 240° F., about 220° F. to about 260° F., about 240° F. to about 280° F., about 260° F. to about 300° F., about 280° F. to about 320° F., about 300° F. to about 340° F., about 320° F. to about 360° F., about 340° F. to about 380° F., about 360° F. to about 400° F., about 380° F. to about 420° F., or about 400° F. to about 440° F. Cooling the gas stream may comprise cooling the gas stream to about −100 to about −50° F., about −50 to about −25° F., about −25 to about 0° F., about 0 to about 25° F., about 25 to about 50° F., about 50 to about 75° F., or about 75 to about 100° F.

The method may further comprise heating the gas stream and/or extraction chamber to a temperature higher than the boiling point of at least one molecule of the portion of oil, e.g., thereby facilitating volatilization. Such a temperature may be, for example, about 315° F., about 356° F., or about 428° F. The temperature higher than the boiling point may be about 300° F., about 305° F., about 310° F., about 315° F., about 320° F., about 325° F., about 330° F., about 335° F., about 340° F., about 345° F., about 350° F., about 355° F., about 360° F., about 365° F., about 370° F., about 375° F., about 380° F., about 385° F., about 390° F., about 395° F., about 400° F., about 405° F., about 410° F., about 415° F., about 420° F., about 425° F., about 430° F., about 435° F., about 440° F., about 445° F., about 450° F., or about 460° F. In some embodiments, the at least one molecule may comprise cannabidiol (CBD), cannabidivarin (CBDV), cannabigerol (CBG), delta-9-tetrahydrocannabinol (THC), delta-8-tetrahydrocannabinol, tetrahydrocannabivarin (THCV), cannabinol (CBN), cannabigerol, cannabichromene, a chemically converted cannabinoid, any other cannabinoid, any other terpene or terpenoid, linalool, caryophyllene, myrcene, limonene, humulene, and/or pinene.

The plant material may comprise hemp or cannabis. For example, the plant material may comprise *Cannabis sativa, Cannabis indica, Cannabis ruderalis,* a hybridized cross of a species or family of cannabis, or a combination of two or more of the foregoing.

In some embodiments, the portion of oil and/or collected oil comprises cannabidiol (CBD), cannabidivarin (CBDV), cannabigerol (CBG), delta-9-tetrahydrocannabinol (THC), delta-8-tetrahydrocannabinol, tetrahydrocannabivarin (THCV), cannabinol (CBN), cannabigerol, cannabichromene, a chemically converted cannabinoid, any other cannabinoid, any other terpene or terpenoid, linalool, caryophyllene, myrcene, limonene, humulene, pinene, or a combination of two or more of the foregoing. For example, the portion of oil and/or collected oil may comprise delta-9-tetrahydrocannabinol (THC), e.g., at a weight percentage of at least about 10%, 15%, 20%, 25%, 30%, 35%, 40%, 45%, 50%, 55%, 60%, 65%, 70%, 75%, 80%, 85%, 90%, 95%, or about 99%. The portion of oil and/or collected oil may comprise cannabidiol (CBD), e.g., at a weight percentage of at least about 10%, 15%, 20%, 25%, 30%, 35%, 40%, 45%, 50%, 55%, 60%, 65%, 70%, 75%, 80%, 85%, 90%, 95%, or about 99%.

Those of skill in the art will recognize that the herein described embodiments of the present invention may be altered in other ways without departing from the scope or teaching of the present invention. As such, this disclosure should be interpreted broadly.

The invention claimed is:

1. A method of extracting oil from plant material, comprising:
providing a system for extracting oil from plant material, wherein the system comprises (a) a gas moving device operable to propel a gas stream through the system, (b) an extraction chamber in communication with the gas moving device such that the gas stream is directed through the extraction chamber, and (c) a centrifugal separator comprising a condensation surface in communication with the gas moving device such, that the gas stream is directed to the condensation surface;
providing a plant material in the extraction chamber;
propelling the gas stream through the extraction chamber to entrain the plant material in the gas stream;
volatizing an oil from the plant material that is entrained in the gas stream such that the oil is extracted from the plant material and into the gas stream;
cooling the gas stream containing the oil;
propelling the gas stream containing the oil to the centrifugal separator;
contacting the gas stream with the condensation surface of the centrifugal separator hereby capturing and removing a portion of the oil from the gas stream; and
collecting the portion of the oil from the condensation surface thereby producing a collected oil,
wherein:
the gas stream comprises less than 25% solvent vapor by weight;
the portion of the oil captured and removed from the gas stream comprises less than 25% solvent by weight; and
the collected oil comprises less than 25% solvent by weight.

2. A method of extracting oil from plant material, comprising:
providing a system for extracting oil from plant material, wherein the system comprises (a) a gas moving device operable to propel a gas stream through the system, (b) an extraction chamber in communication with the gas moving device such that the gas stream is directed through the extraction chamber, and (c) a condensation surface in communication with the gas moving device such that the gas stream is directed to the condensation surface;
providing a plant material in the extraction chamber;
propelling the gas stream through the extraction chamber to entrain the plant material in the gas stream;
volatizing an oil from the plant material that is entrained in the gas stream such that the oil is extracted from the plant material and into the gas stream;
cooling the gas stream containing the oil;
propelling the gas stream containing the oil to the condensation surface;
contacting the gas stream with the condensation surface thereby capturing and removing a portion of the oil from the gas stream;
maintaining the condensation surface at an angle and temperature that result in a parallel component of gravitational force that is greater than the resistance of the portion of the oil to flow; and
collecting the portion of the oil from the condensation surface thereby producing a collected oil,
wherein:

the gas stream comprises less than 25% solvent vapor by weight;

the portion of the oil captured and removed from the gas stream comprises less than 25% solvent by weight; and the collected oil comprises less than 25% solvent by weight.

3. The method of claim 2, comprising maintaining the condensation surface at an angle of about −90° to about 60° relative to the force of gravity, wherein:

surfaces of less than 0° to about −90° are ceilings;

a surface of 0° is a wall that is parallel to the force of gravity; and surfaces of greater than 0° to less than 90° are inclined planes.

4. The method of claim 3, comprising maintaining the condensation surface at an angle of about −45° to about 45° relative to the force of gravity.

5. The method of claim 2, comprising maintaining the temperature of the condensation surface at about 100 to about 300° F., about 110 to about 289° F., about 120 to about 280° F., about 120 to about 150° F., about 290 to about 314° F., about 316 to about 355° F., about 320 to about 340° F., about 357 to about 364° F., or about 366 to about 427° F.

6. A method of extracting oil from plant material, comprising:

providing a system for extracting oil from plant material, wherein the system comprises (a) a gas moving device operable to propel a gas stream through the system, (b) an extraction chamber in communication with the gas moving device such that the gas stream is directed through the extraction chamber, and (c) a condensation surface in communication with the gas moving device such that the gas stream is directed to the condensation surface;

providing a plant material in the extraction chamber;

propelling the gas stream through the extraction chamber to entrain the plant material in the gas stream;

volatizing an oil from the plant material that is entrained in the gas stream such that the oil is extracted from the plant material and into the gas stream;

cooling the gas stream containing the oil;

contacting the gas stream with the condensation surface, wherein the condensation surface comprises an electrostatic charge sufficient to capture and remove a portion of the oil from the gas stream; and collecting the portion of the oil from the condensation surface thereby producing a collected oil, wherein:

the gas stream comprises less than 25% solvent vapor by weight;

the portion of the oil captured and removed from the gas stream comprises less than 25% solvent, by weight; and the collected oil comprises less than 25% solvent by weight.

7. The method of claim 2, wherein cooling the gas stream containing the oil comprises cooling the gas stream to about 100 to about 300° F., about 110 to about 289° F., about 120 to about 280° F., about 120 to about 150° F., about 290 to about 314° F., about 316 to about 355° F., about 320 to about 340° F., about 357 to about 364° F., or about 366 to about 427° F.

8. The method of claim 7, wherein cooling the gas stream containing the oil comprises cooling the gas stream to a temperature that is at least about 5° F., 10° F., 15° F., 20° F., 25° F., 30° F., 35° F., 40° F., 45° F., or 50° F. lower than the temperature of the condensation surface.

9. The method of claim 7, wherein cooling the gas stream containing the oil comprises cooling the gas stream to a temperature that is at least about 5° F., 10° F., 15° F., 20° F., 25° F., 30° F., 35° F., 40° F., 45° F., or 50° F. higher than the temperature of the condensation surface.

10. The method of claim 7, wherein cooling the gas stream containing the oil comprises cooling, the gas stream to a temperature that is about the same temperature as the temperature of the condensation surface.

11. The method of claim 2, further comprising changing the temperature of the condensation surface.

12. The method of claim 11, wherein either:

changing the temperature of the condensation surface comprises increasing the temperature of the condensation surface, and the temperature is increased to decrease the resistance of the portion of the oil to flow; or changing the temperature of the condensation surface comprises decreasing the temperature of the condensation surface, and the temperature is decreased to increase a rate at which the portion of oil is captured and removed from the gas stream.

13. The method of claim 2, further comprising heating the gas stream to a temperature higher than the boiling point of at least one molecule of the portion of oil.

14. The method of claim 2, further comprising heating the extraction chamber to a temperature higher than the boiling point of at least one molecule of the portion of oil.

15. The method claim 13, wherein the temperature higher than the boiling point is about 315° F. about 356° F., or about 428° F.

16. The method of claim 13, wherein the at least one molecule comprises cannabidiol, cannabidivarin, cannabigerol, delta-9-tetrahydrocannabinol, delta-8-tetrahydrocannabinol, or tetrahydrocannabivarin.

17. The method of claim 2, wherein the gas stream, portion of the oil, or collected oil is essentially free of solvent.

18. The method of claim 17, wherein the gas stream, portion of the oil, or collected oil comprises no solvent.

19. The method of claim 18, wherein the gas stream, portion of the oil, or collected oil is essentially free of isobutane, ethanol, or chloroform.

20. The method of claim 2, wherein the plant material comprises hemp or cannabis.

21. The method of claim 2, wherein the portion of oil and collected oil comprises cannabidiol, cannabidivarin, delta-9-tetrahydrocannabinol, delta-8-tetrahydrocannabinol, tetrahydrocannabivarin, cannabigerol, cannabichromene, a chemically converted cannabinoid, any other cannabinoid, linalool, caryophyllene, myrcene, limonene, humulene, pinene, or a combination of two or more of the foregoing.

22. The method of claim 21, wherein the portion of oil and collected oil comprises delta-9-tetrahydrocannabinol.

23. The method of claim 22, wherein the portion of oil and collected oil comprises cannabidiol.

* * * * *